(12) United States Patent
Pak et al.

(10) Patent No.: US 11,931,366 B2
(45) Date of Patent: Mar. 19, 2024

(54) COMPOSITIONS AND METHODS OF USE THEREOF FOR TREATMENT OF PROTEINOPATHIES

(71) Applicant: Washington University, St. Louis, MO (US)

(72) Inventors: Stephen Pak, St. Louis, MO (US); David Perlmutter, St. Louis, MO (US); Gary Silverman, St. Louis, MO (US)

(73) Assignee: Washington University, St. Louis, MO (US)

( * ) Notice: Subject to any disclaimer, the term of this patent is extended or adjusted under 35 U.S.C. 154(b) by 283 days.

(21) Appl. No.: 17/048,957

(22) PCT Filed: Apr. 19, 2019

(86) PCT No.: PCT/US2019/028374
§ 371 (c)(1),
(2) Date: Oct. 19, 2020

(87) PCT Pub. No.: WO2019/204764
PCT Pub. Date: Oct. 24, 2019

(65) Prior Publication Data
US 2021/0228591 A1 Jul. 29, 2021

Related U.S. Application Data

(60) Provisional application No. 62/749,854, filed on Oct. 24, 2018, provisional application No. 62/660,056, filed on Apr. 19, 2018.

(51) Int. Cl.
| | | |
|---|---|---|
| A61K 31/5415 | (2006.01) | |
| A61K 31/135 | (2006.01) | |
| A61K 31/138 | (2006.01) | |
| A61K 31/155 | (2006.01) | |
| A61K 31/4418 | (2006.01) | |
| A61K 31/444 | (2006.01) | |
| A61K 31/4453 | (2006.01) | |
| A61K 31/505 | (2006.01) | |
| A61K 31/5355 | (2006.01) | |
| A61K 31/7135 | (2006.01) | |
| A61K 45/06 | (2006.01) | |
| A61P 43/00 | (2006.01) | |

(52) U.S. Cl.
CPC ........ *A61K 31/5415* (2013.01); *A61K 31/135* (2013.01); *A61K 31/138* (2013.01); *A61K 31/155* (2013.01); *A61K 31/4418* (2013.01); *A61K 31/444* (2013.01); *A61K 31/4453* (2013.01); *A61K 31/505* (2013.01); *A61K 31/5355* (2013.01); *A61K 31/7135* (2013.01); *A61K 45/06* (2013.01); *A61P 43/00* (2018.01)

(58) Field of Classification Search
CPC .................................. A61K 31/55; A61P 9/10
See application file for complete search history.

(56) References Cited

U.S. PATENT DOCUMENTS

2017/0105999 A1* 4/2017 Huang et al. ............. A61P 1/04

FOREIGN PATENT DOCUMENTS

WO WO-2016062266 A1 * 4/2016 ........... A61K 31/085

OTHER PUBLICATIONS

By Li et al., "Fluphenazine Reduces Proteotoxicity in C. elegens and Mammalian Models of Alpha-1-Antitrypsin Deficiency", PLoS One, vol. 9, No. 1, pp. e87260 (2014).*

* cited by examiner

*Primary Examiner* — Kevin E Weddington
(74) *Attorney, Agent, or Firm* — Polsinelli PC

(57) ABSTRACT

The present disclosure relates generally compositions and methods of using the same for the treatment of proteinopathies (e.g. Alpha-1-antitrypsin deficiency, Non-alcoholic fatty liver disease, Alzheimer's disease, Parkinson's disease, Amyotrophic Lateral Sclerosis, and Huntington's disease) with one or more proteotoxicity reducing agents.

7 Claims, 18 Drawing Sheets
(12 of 18 Drawing Sheet(s) Filed in Color)

| ATZ Pathology | Human | *C. elegans* |
|---|---|---|
| 1. formation of polymers | √ | √ |
| 2. ER retention | √ | √ |
| 3. impaired secretion | √ | √ |
| 4. autophagic clearance | √ | √ |
| 5. reduced life span | √ | √ |
FIG. 2A
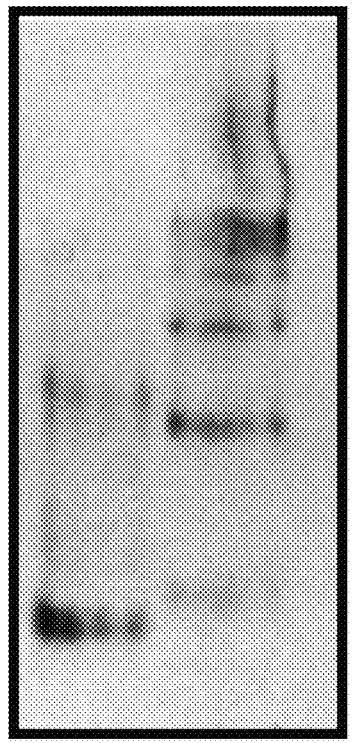
FIG. 2B
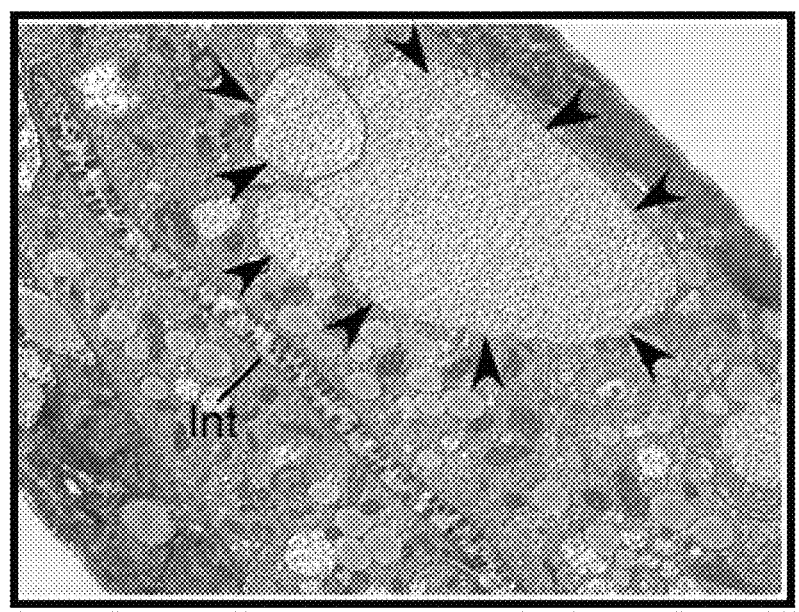
FIG. 2C

| Drug A (3.3 pM) | − | − | + | + | − | − | + | + |
| Drug B (100 pM) | − | − | − | − | + | + | + | + |

COMPOSITIONS AND METHODS OF USE THEREOF FOR TREATMENT OF PROTEINOPATHIES

CROSS REFERENCE TO RELATED APPLICATIONS

This application claims the benefit of International Patent Application number PCT/US2019/028374, filed Apr. 19, 2019 which claims the benefit of U.S. Provisional Application No. 62/660,056, filed Apr. 19, 2018 and U.S. Provisional Application No. 62/749,854, filed Oct. 24, 2018 the disclosures of which are herein incorporated by reference in their entirety.

GOVERNMENTAL RIGHTS

This invention was made with government support under DK096990 awarded by the National Institutes of Health. The government has certain rights in the invention.

FIELD OF THE TECHNOLOGY

The present disclosure relates to compositions and methods of using the same for the treatment of proteinopathies (e.g. Alpha-1-antitrypsin deficiency, Non-alcoholic fatty liver disease, Alzheimer's disease, Parkinson's disease, Amyotrophic Lateral Sclerosis, and Huntington's disease).

BACKGROUND

Proteinopathy refers to a class of diseases in which certain proteins become structurally abnormal, and thereby disrupt the function of cells, tissues and organs of the body. Often the proteins fail to fold into their normal configuration; in this misfolded state, the proteins can become toxic in some way (a gain-of-toxic function) or they can lose their normal function. The proteinopathies (also known as proteinopathies, protein conformational disorders, or protein misfolding diseases) include such diseases as Alpha-1-antitrypsin deficiency, Alzheimer's disease, Parkinson's disease, Amyotrophic lateral sclerosis, Huntington's disease, amyloidosis, and a wide range of other disorders.

Proteinopathies appear, at the clinical level, to be a diverse group of disorders encompassing many diseases, from late-onset neurodegenerative disorders through to forms of heart failure. These conditions are unified by the common feature of accumulation of misfolded proteins. A change in 3-dimensional folding (conformation) increases the tendency of a specific protein to bind to itself. In this aggregated form, the protein is resistant to clearance and can interfere with the normal capacity of the affected organs. In some cases, misfolding of the protein results in a loss of its usual function. The specific protein, cell type and cellular localization of these accumulations vary between the diseases. For example, Parkinson's disease is characterized by the presence of cytoplasmic aggregates of α-synuclein, whereas in the polyglutamine expansion disorders, aggregates are seen predominantly within the nucleus in spinocerebellar ataxia type 1, or in the cytoplasm in adult-onset Huntington's disease. In Alzheimer's disease (AD), both intracellular tau aggregates and extracellular amyloid-β (Aβ) aggregates are seen.

The possibility of a common mechanism underlying either the pathogenesis or therapy for these diseases is appealing. There is great interest in the role of protein degradation via autophagy in such conditions where the protein is found in the cytoplasm. Autophagy is an intracellular process in which cytoplasmic materials are engulfed by double membrane structures, which form autophagosomes. The autophagosomes first fuse with endosomes to form hybrid organelles called amphisomes that later fuse with lysosomes, where the entrapped cytosolic contents are degraded. The process of autophagy has been proposed to be important in protein misfolding disorders, both as a contributing factor, through inhibition of the process, and a potential therapeutic strategy, through its upregulation Alpha-1-antitrypsin deficiency (ATD) is a proteinopathy affecting approximately 3.4 million individuals worldwide. Individuals with ATD are predisposed to liver disease (e.g., cirrhosis and hepatocellular carcinoma) and chronic lung disease (e.g., emphysema). ATD is the leading genetic cause of pediatric liver transplants and the leading genetic cause of emphysema in adults. Individuals with ATD have only a 16% likelihood of surviving to age 60 years (in contrast to 85% for the general population). The societal cost for ATD is estimated to be in excess of 2 billion dollars in the US alone. While replacement/augmentation therapy is currently prescribed for the treatment of chronic lung disease due to ATD, no effective treatment currently exists for the liver disease except for liver transplantation. Of the approximately 3.4 million individuals with ATD, approximately 10-15% (or 500,000 individuals) will develop severe liver disease characterized by neonatal hepatitis and juvenile cirrhosis in the first two decades of life. Another 20-30% (or 1 million individuals) will develop clinically significant liver disease characterized by cirrhosis, gastrointestinal bleeding, hepatic encephalopathy and hepatocellular carcinoma later in life. Currently there is no effective treatment except for full liver transplantation.

In addition to the liver disease, ~50-60% (or 2 million individuals) with ATD will develop chronic lung disease characterized by emphysema. Lung disease is widely thought to be due to the lack of circulating AT (or loss-of-AT-function). As such, replacement or augmentation therapy is currently prescribed for individuals with signs of lung disease. This therapy was approved by the FDA based purely on biochemical (not clinical) evidence and there is ongoing debate regarding the therapy's efficacy. ATD patients with chronic lung disease require once weekly injections of purified human AT for the entire duration of life. The cost of replacement therapy is ~$40,000/person/year.

Therefore a need exists in the art for a safe and effective therapeutic that mitigates ATD induced liver and lung disease and has a significant impact on improving the lives of individuals with ATD.

SUMMARY

Among the various aspects of the present disclosure provide methods and pharmaceutical compositions comprising an effective amount of a proteotoxicity reducing agent, for use in treating conditions associated with a proteinopathy.

In an aspect of the disclosure provides method for treating alpha-1-antitrypsin deficiency (ATD) in a subject in need thereof comprising administering to the subject a therapeutically effective amount of one or more a proteotoxicity reducing agent. In some embodiments the one or more proteotoxicity reducing agent comprises Prochlorperazine and Amlodipine. In some embodiments the one or more proteotoxicity reducing agent comprises Prochlorperazine and Nilvadipine. In some embodiments the one or more proteotoxicity reducing agent comprises Prochlorperazine and Alexidine. In some embodiments the one or more proteotoxicity reducing agent comprises Prochlorperazine and Chlorhexidine. In some embodiments the one or more proteotoxicity reducing agent comprises Prochlorperazine and Hexetidine. In some embodiments the one or more proteotoxicity reducing agent comprises Prochlorperazine and Auranofin. In some embodiments the one or more proteotoxicity reducing agent comprises Prochlorperazine and Sertraline. In some embodiments the one or more proteotoxicity reducing agent comprises Prochlorperazine and Toremifene. In some embodiments the one or more proteotoxicity reducing agent comprises Prochlorperazine and Perhexiline. In some embodiments the one or more proteotoxicity reducing agent comprises Prochlorperazine and Aprepitant. In some embodiments the one or more proteotoxicity reducing agent comprises Prochlorperazine and Desloratadine. In some embodiments the one or more proteotoxicity reducing agent comprises Prochlorperazine and Amlodipine. In some embodiments the one or more proteotoxicity reducing agent comprises Desloratadine and Amlodipine. In some embodiments the one or more proteotoxicity reducing agent comprises Amlodipine and Perhexiline.

In a further aspect the disclosure provides a method for treating a proteinopathy in a subject in need thereof comprising administering to the subject a therapeutically effective amount of one or more of a proteotoxicity reducing agent. In some embodiments the one or more proteotoxicity reducing agent comprises Prochlorperazine and Amlodipine. In some embodiments the one or more proteotoxicity reducing agent comprises Prochlorperazine and Nilvadipine. In some embodiments the one or more proteotoxicity reducing agent comprises Prochlorperazine and Alexidine. In some embodiments the one or more proteotoxicity reducing agent comprises Prochlorperazine and Chlorhexidine. In some embodiments the one or more proteotoxicity reducing agent comprises Prochlorperazine and Hexetidine. In some embodiments the one or more proteotoxicity reducing agent comprises Prochlorperazine and Auranofin. In some embodiments the one or more proteotoxicity reducing agent comprises Prochlorperazine and Sertraline. In some embodiments the one or more proteotoxicity reducing agent comprises Prochlorperazine and Toremifene. In some embodiments the one or more proteotoxicity reducing agent comprises Prochlorperazine and Perhexiline. In some embodiments the one or more proteotoxicity reducing agent comprises Prochlorperazine and Aprepitant. In some embodiments the one or more proteotoxicity reducing agent comprises Prochlorperazine and Desloratadine. In some embodiments the one or more proteotoxicity reducing agent comprises Prochlorperazine and Amlodipine. In some embodiments the one or more proteotoxicity reducing agent comprises Desloratadine and Amlodipine. In some embodiments the one or more proteotoxicity reducing agent comprises Amlodipine and Perhexiline.

In another aspect the disclosure provides a method for treating a ATD or proteinopathy in a subject in need thereof comprising administering to the subject a therapeutically effective amount of a tricyclic antipsychotic and a vasodilator.

In still another aspect the disclosure provides a method for treating a ATD or proteinopathy in a subject in need thereof comprising administering to the subject a therapeutically effective amount of a tricyclic antipsychotic and an antibiotic/antiseptic.

In yet another aspect the disclosure provides a method for treating a ATD or proteinopathy in a subject in need thereof comprising administering to the subject a therapeutically effective amount of a tricyclic antipsychotic and an antidepressant.

While multiple embodiments are disclosed, still other embodiments of the present invention will become apparent to those skilled in the art from the following detailed description, which shows and describes illustrative embodiments of the invention.

BRIEF DESCRIPTION OF THE FIGURES

Those of skill in the art will understand that the drawings, described below, are for illustrative purposes only. The drawings are not intended to limit the scope of the present teachings in any way.

The application file contains at least one drawing executed in color. Copies of this patent application publication with color drawing(s) will be provided by the Office upon request and payment of the necessary fee.

FIG. 1A shows transgenic *C. elegans* expressing human wild-type alpha-1-antitrypsin (AT) gene fused to green fluorescent protein (GFP). Wild-type AT is efficiently processed by the cells and there is no accumulation. FIG. 1B shows a liver section from normal mouse showing no accumulation of AT. FIG. 1C shows a transgenic *C. elegans* expressing human mutant alpha-1-antitrypsin gene fused to GFP. Mutant AT accumulates as large protein polymers/aggregates. FIG. 1D shows a liver section from a mouse with alpha-1-antitrypsin deficiency (ATD) stained with PA showing extensive accumulation of mutant AT in hepatocytes (magenta spots).

FIG. 2A, FIG. 2B, FIG. 2C, FIG. 2D, FIG. 2E and FIG. 2F depict the characterization of the *C. elegans* model of ATD liver disease. FIG. 2A shows comparison of phenotypes between human and *C. elegans* disease model. The *C. elegans* model faithfully recapitulates important aspects of the human disease. FIG. 2B shows a native PAGE analysis of *C. elegans* lysates from transgenic animals expressing wildtype (lane 1) and mutant (lane 2) AT protein. Mutant, but not wild-type, lysate shows presence of high order polymers. FIG. 2C shows an electron micrograph of a *C. elegans* intestine showing accumulation of mutant AT protein in the endoplasmic reticulum (black arrowheads). FIG. 2D shows a fluorescent image of a transgenic animal expressing mutant AT protein. Mutant AT protein secretion is impaired as indicated by the intracellular accumulation of the protein (red arrows). FIG. 2E depicts the autophagy pathway used by the cells to clear mutant AT protein. FIG. 2F shows lifespans of transgenic *C. elegans* expressing wild-type and mutant AT proteins. Animals expressing wild-type AT (blue curve) have a normal lifespan similar to non-transgenic animals (black curve). In contrast, animals expressing mutant AT have a significantly shorter lifespan (red curve).

FIG. 4A shows examples of hit compounds—fluphenazine, perphenazine, prochlorperazine and trifluoperazine. FIG. 4B shows an 8-point dose response curve of fluphenazine showing dose-dependent reduction of mutant AT in the *C. elegans* model.

FIG. 5A, shows dose response of fluphenazine.

FIG. 5B, shows dose response of prochlorperazine. FIG. 5C, shows dose response of thiethylperazine. FIG. 5D, shows dose response of perphenazine. FIG. 5E, shows dose response of trifluoperazine. FIG. 5F, shows dose response of thioridazine.

FIG. 6A shows the genetic details of the transgenic mouse model of ATD. FIG. 6B shows liver sections from mice treated with control (CTR) or fluphenazine (FLU) treated mice. Liver sections from mice treated with fluphenazine show significantly reduced accumulation of mutant AT protein (purple dots). FIG. 6C shows quantification of AT accumulations. The percent area of purple dots is significantly reduced in fluphenazine treated mice.

FIG. 7A shows Sirius red stained liver sections from mice treated with control (CTR) or fluphenazine (FLU). Sirius red staining indicates presence of collagen deposition indicative of liver fibrosis. Sirius red staining is significantly reduced in mice treated with fluphenazine (FLU). FIG. 7B shows quantification of Sirius red staining showing significant reduction of fibrosis in mice treated with fluphenazine (FLU).

FIG. 8A, FIG. 8B, and FIG. 8C depicts autophagy as the mechanism of fluphenazine mediated clearance of mutant AT. FIG. 8A shows a schematic of the autophagy pathway and the role of LC3 and p62. FIG. 8B shows an increase in the LC3-II/I ratio following fluphenazine treatment (purple bar). FIG. 8C shows a reduction of p62 following fluphenazine treatment (orange bar). Taken together these results indicate that fluphenazine works by enhancing autophagic flux

FIG. 10A shows a checkerboard analysis of amlodipine and prochlorperazine at various doses. FIG. 10B shows an isobologram analysis which is a gold standard in determining drug combination synergy. Amlodipine and prochlorperazine combinations at various doses were shown to be synergistic. FIG. 10C shows western blot of cells expressing mutant AT treated with amlodipine (Drug A) and/or prochlorperazine (Drug B). Top panel shows AT protein and bottom panel shows actin (loading control). Cells treated with Drug A and Drug B (last 2 lanes) show greater reduction of mutant AT than cells treated with Drug A or Drug B alone.

FIG. 11A shows RDR 03172 reducing AT accumulations in a dose-dependent manner. FIG. 11B shows AW00794 reduces AT accumulation.

DETAILED DESCRIPTION

Figure 1A:
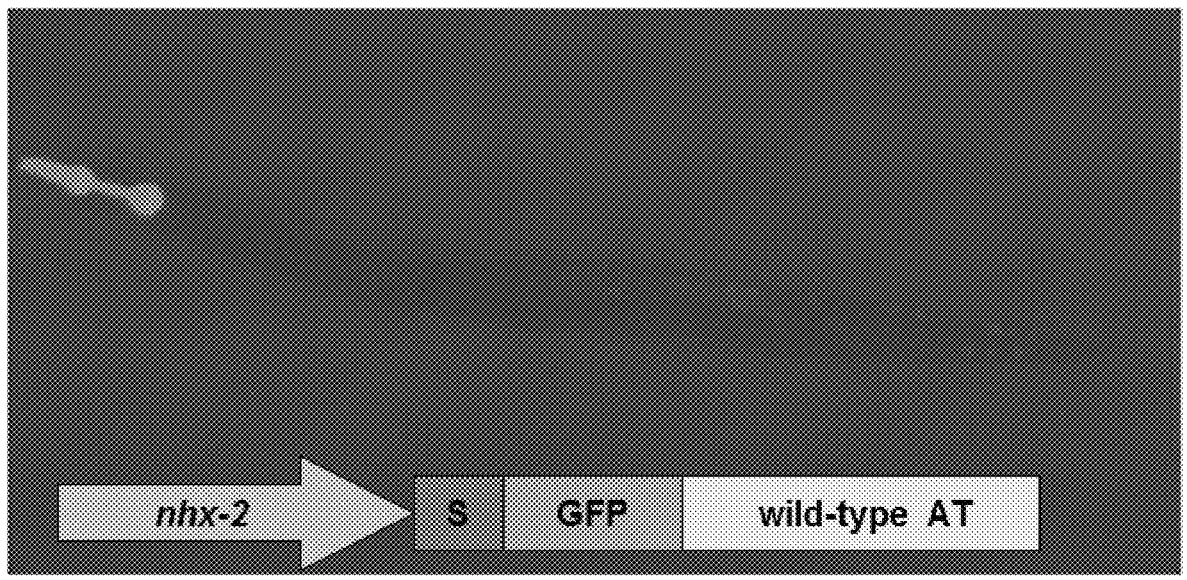
FIG. 1A, FIG. 1B, FIG. 1C and FIG. 1D depict the *C. elegans* model of ATD.
Figure 1B:
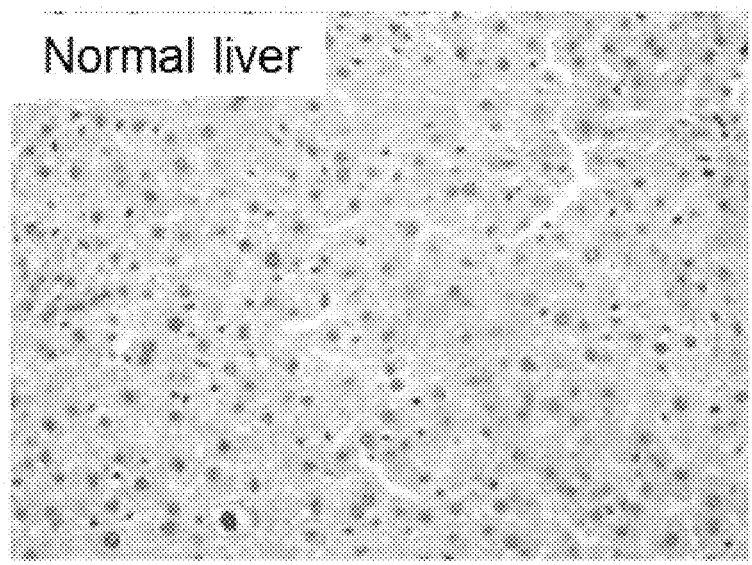
Figure 1C:
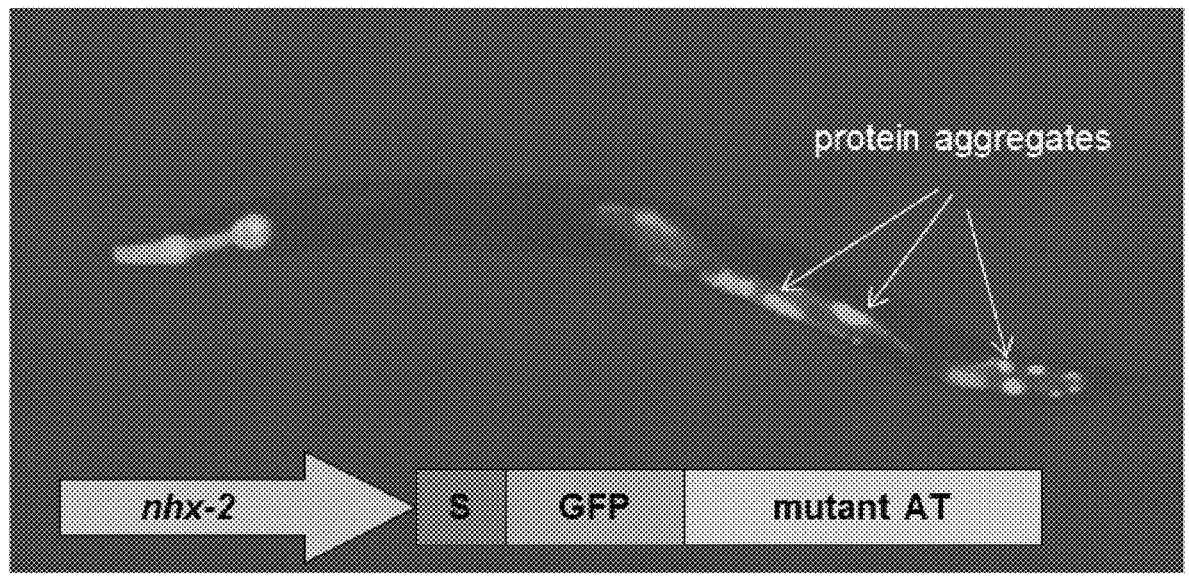
Figure 1D:
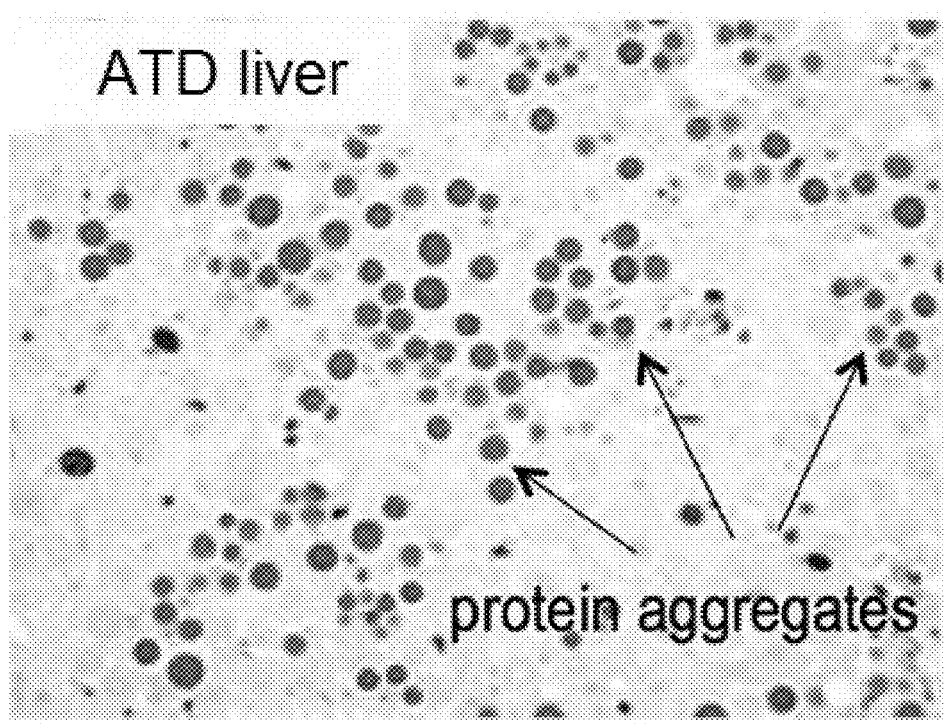
Figure 2D:
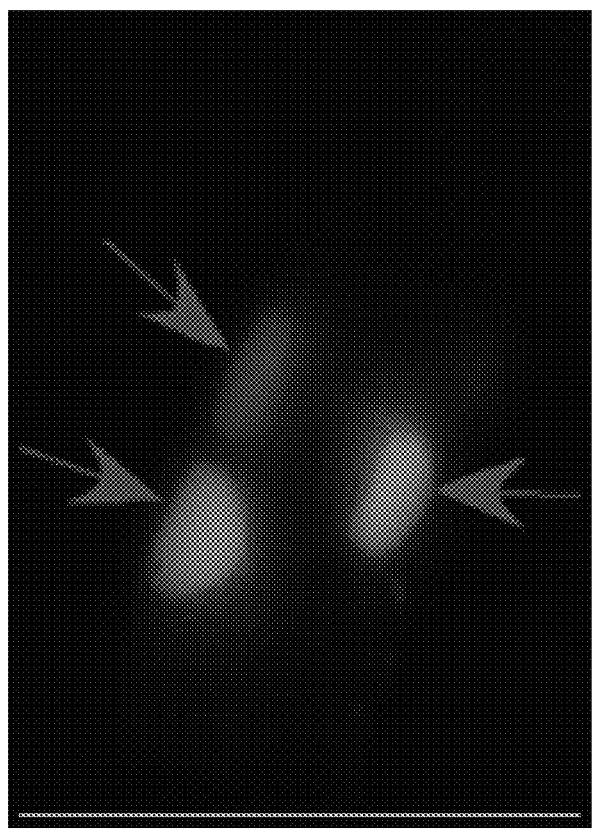
Figure 2E:
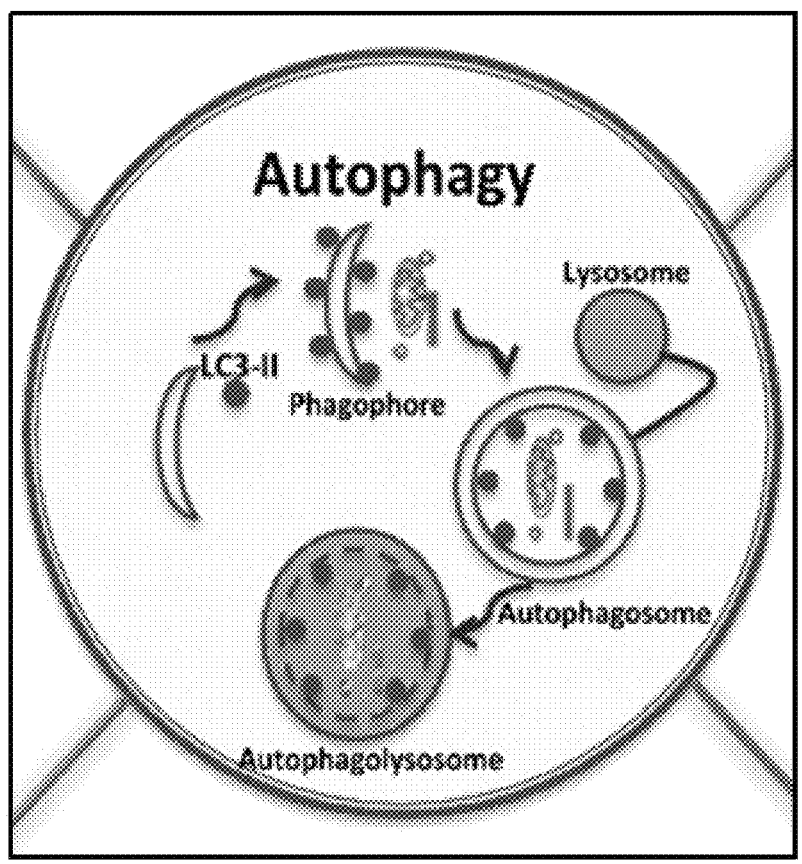
Figure 2F:
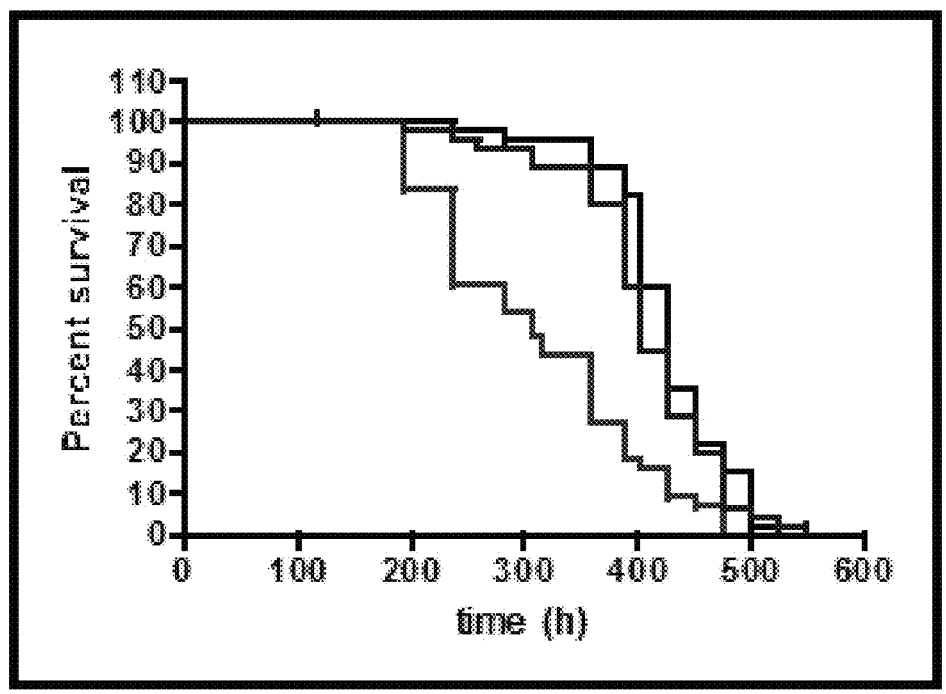
Figure 3:
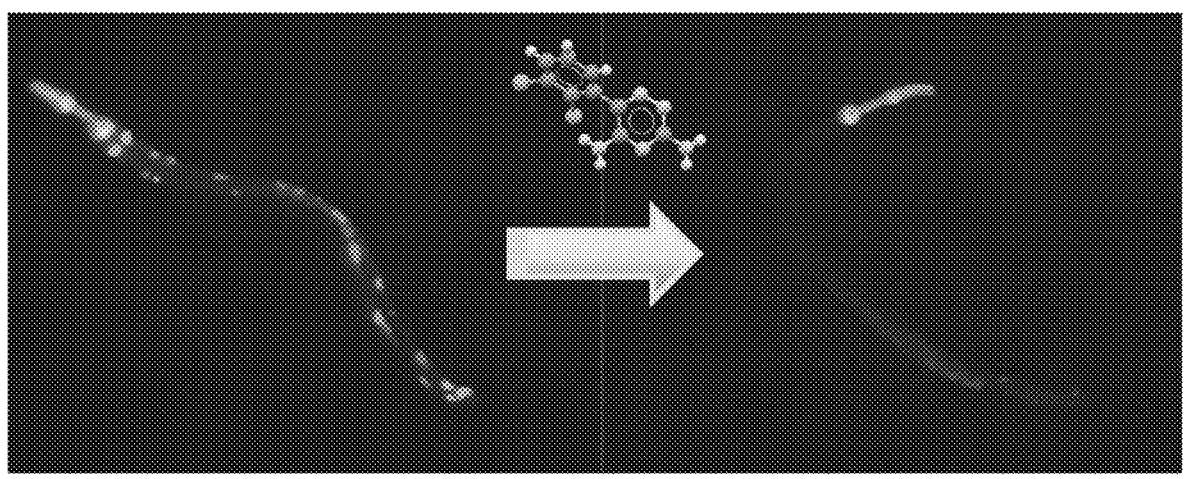
FIG. 3 depicts the phenotypic screening strategy to identify drugs that reduce mutant AT accumulation in *C. elegans*.
Figure 4A:
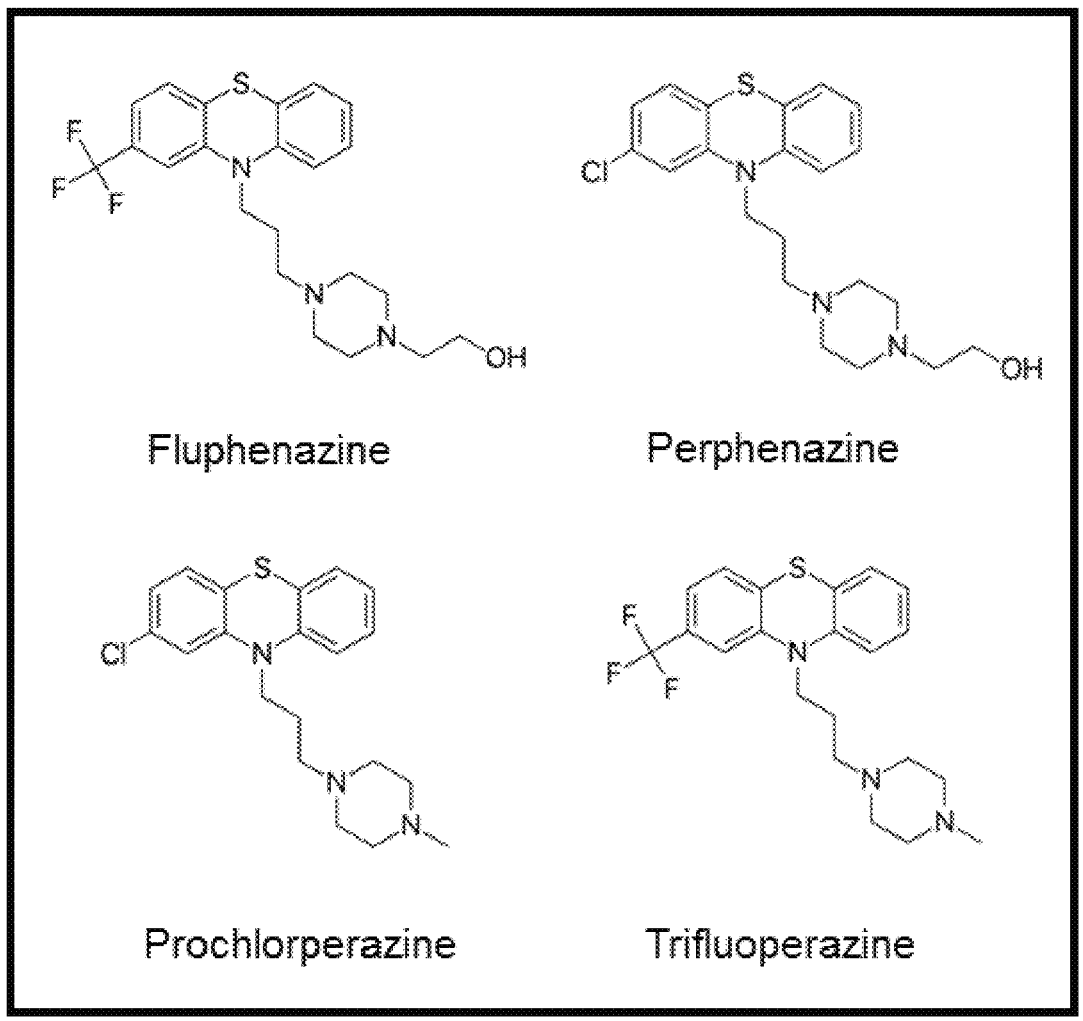
FIG. 4A and FIG. 4B shows selected results from the high-throughput screening campaign.
Figure 4B:
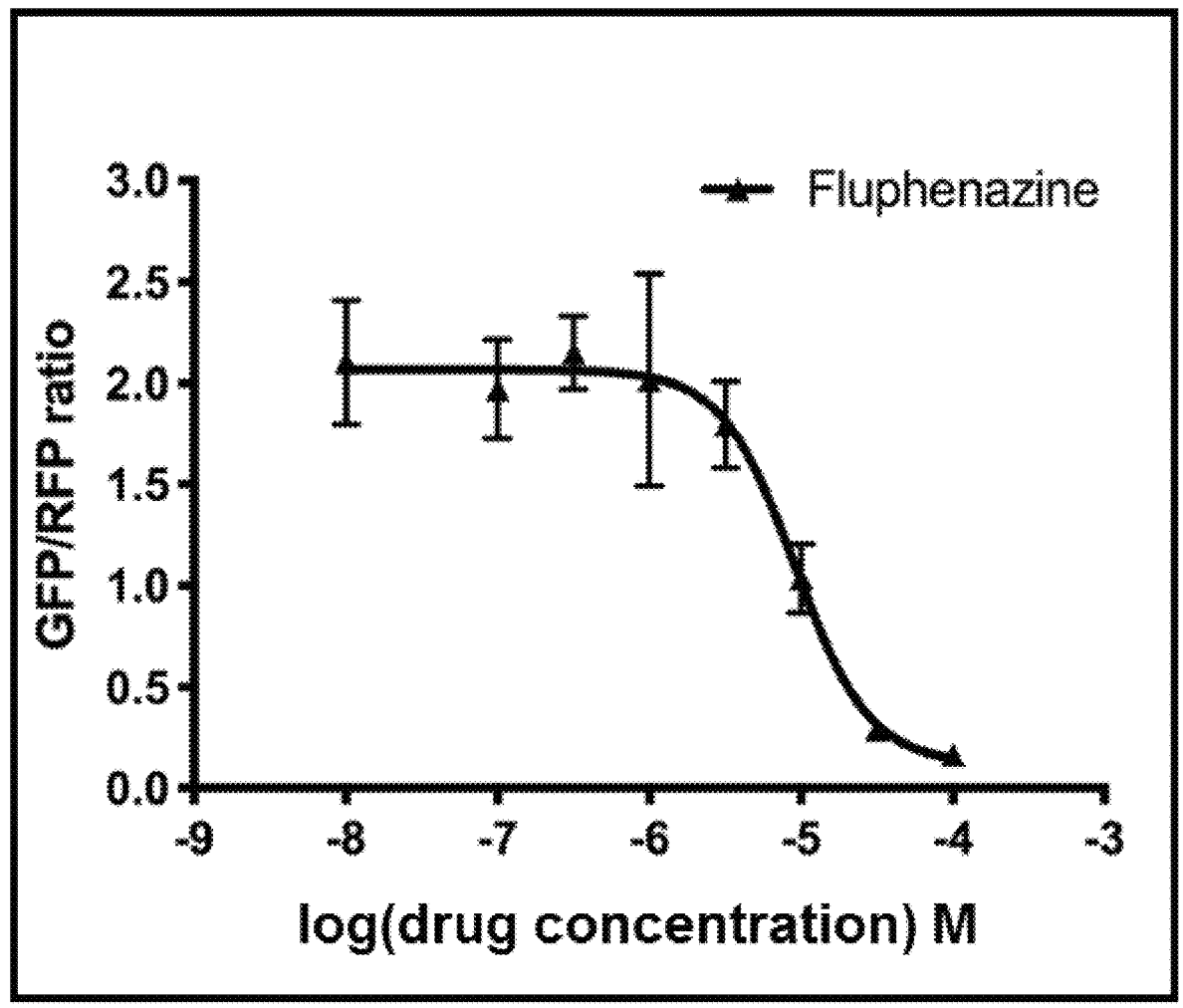

The present disclosure is based, at least in part, on the discovery of drugs and combinations thereof which work to reduce proteotoxicity associated with various proteinopathies. As such, the present disclosure provides new compositions, uses, and techniques for treating proteinopathies, such as, Alpha-1-antitrypsin deficiency, Non-alcoholic fatty liver disease, Alzheimer's disease, Parkinson's disease, Amyotrophic Lateral Sclerosis, and Huntington's disease. These compositions and methods can be useful to correct cell and organ dysfunction caused by primary abnormalities in protein aggregation and accumulation. In particular, the compositions and methods can be useful to reduce misfolded/mutant protein accumulation in a target organ, enhance clearance of a misfolded/mutant protein from a target organ/cell and/or enhance autophagy in a cell or subject in need thereof.

The present disclosure identifies major classes of drugs (Tricyclic antipsychotics, Vasodilators, Antibiotics/Antiseptics, and Aryl piperazines) administered alone or in combination are useful in the compositions and methods for treatment of various proteinopathies. Moreover, combinations of these drugs are shown to act synergistically to reduce proteotoxicity, thereby provide improved efficacy, lower individual drug doses and reduced side effects. Drug classes were identified using a live animal-based high-throughput screening (HTS) platform. The use of a live-animal in drug screening provides significant advantages by allowing simultaneous assessment of systemic drug toxicity and efficacy (and bioavailability). The dual read-out system eliminates nuisance compounds early in the screening process and increases identification of efficacious human drugs. As described herein, drug efficacies were tested in the nematode (*C. elegans*), human cell culture and mouse models of ATD. In each of these models, the drugs were able to significantly reduce proteotoxicity associated with ATD. Studies conducted in mice showed significant reversal of liver injury (measured by reduced liver fibrosis) following single drug treatments.

Disclosed are components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Various aspects of the invention are described in further detail in the following sections.

(I) Compositions

One aspect of the present disclosure encompasses one or more proteotoxicity reducing agent or derivatives thereof. A derivative of a proteotoxicity reducing agent, may be modified to improve potency, bioavailability, solubility, stability, handling properties, or a combination thereof, as compared to an unmodified version. Thus, in another aspect, a composition of the invention comprises one or more of a modified proteotoxicity reducing agent. In still another aspect, a composition of the invention comprises a prodrug of a proteotoxicity reducing agent, or prodrug of a derivative of a proteotoxicity reducing agent.

A composition of the invention may optionally comprise one or more additional drug or therapeutically active agent in addition to the one or more of a proteotoxicity reducing agent or derivate thereof. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

Other aspects of the invention are described in further detail below.

a) Proteotoxicity Reducing Agent (i) Tricyclic Antipsychotic/Antihistamine

In one aspect, the compositions detailed herein include a compound comprising a tricyclic antipsychotic. The tricyclic antipsychotic are a group of related compounds which have in common a cyclic chemical structure. These compounds differ in terms of the side-chains which come off of this cyclic structure. Antipsychotics are medications used to treat schizophrenia and manifestations of psychotic disorders. Some antipsychotics, like prochlorperazine and chlorpromazine, are used for nausea, vomiting, and hiccups. Although, the exact mechanism of phenothiazine antipsychotics is unknown, scientists believe that they may work by blocking the action of dopamine in the brain. Phenothiazine antipsychotics are used when patients do not respond to other antipsychotics. The isolation and synthesis of various tricyclic antipsychotic compounds is known in the art and the compounds are also manufactured commercially.

Example of tricyclic antipsychotic drugs include: without being limited thereto, phenothiazine or thioxanthene class of compounds including dibenzodia zepine derivative, or thio phenothiazine derivative and other heterocyclic compounds. Specific examples are prochlorperazine, thioridazine, perphenazine, trifluoperazine or fluphenazine. Specific examples of antipsychotics which are not of the phenothiazine class of agents include flupenthixol. Other non-limiting examples include, acetophenazine, alimemazine, amoxapine, asenapine, butaclamol, butaperazine, carfenazine (carphenazine), carpipramine, chlorpromazine, chlorprothixene, ciclindole, citatepine, clocapramine, clomacran, clorotepine, clotiapine, clozapine, cyanothepin, doclothepin, docloxythepin, erizepine, flucindole, flumezapine, fluotracen, flupentixol, gevotroline, homopipramol, isofloxythepin, levomepromazine/methotrimeprazine, loxapine, lurasidone, maroxepin, meperathiepin, mesoridazine, metiapine, metitepine, metoxepin, mosapramine, naranol, octomethothepin, olanzapine, oxyclothepin, oxyprothepin, pentiapine, peradithiepin, perathiepin, perazine, periciazine, pinoxepin, piperacetazine, pipotiazine, piquindone, promazine, prothipendyl, quetiapine, savoxepin/cipazoxapine, sulforidazine, tenilapine, thiethylperazine, thiopropazate, thiothixene, tilozepine, traboxopine, triflupromazine, trifluthepin, zotepine and zuclopenthixol. Additional examples are those described in Goodman & Gilman, The Pharmacological Basis of Therapeutics, 9th Ed. McGraw-Hill, 1996 herein incorporated by reference in its entirety (See, e.g., Chapter 18, p 404, Table 18-1).

The development of antihistamine drugs began more than 5 decades ago with the discovery that piperoxan was able to protect animals from the bronchial spasm induced by histamine. This finding was followed by the synthesis of a number of N-phenylethylenediamines with antihistaminic activities superior to piperoxan. Further traditional structure-activity studies in this series based largely on the principles of isosterism and functional group modification led to the introduction in the 1940s to 1970s of a variety of $H_1$-antagonists containing the diarylalkylamine framework. Tricyclic antihistamine compounds differ from the phenothiazine antipsychotics in the ring-substitution and chain characteristics. They are also structurally related to the tricyclic antidepressants (and tetracyclics).

Example of tricyclic antihistamine drugs include: without being limited thereto, phenothiazine class of compounds and other heterocyclic compounds. Specific non-limiting example includes desloratadine, cyproheptadine, alimemazine, phenindamine diphenhydramine, olopatadine, rupatadine, ketotifen, and loratadine.

In exemplary embodiments, a compound of the disclosure comprises a tricyclic antipsychotic/antihistamine as shown below:

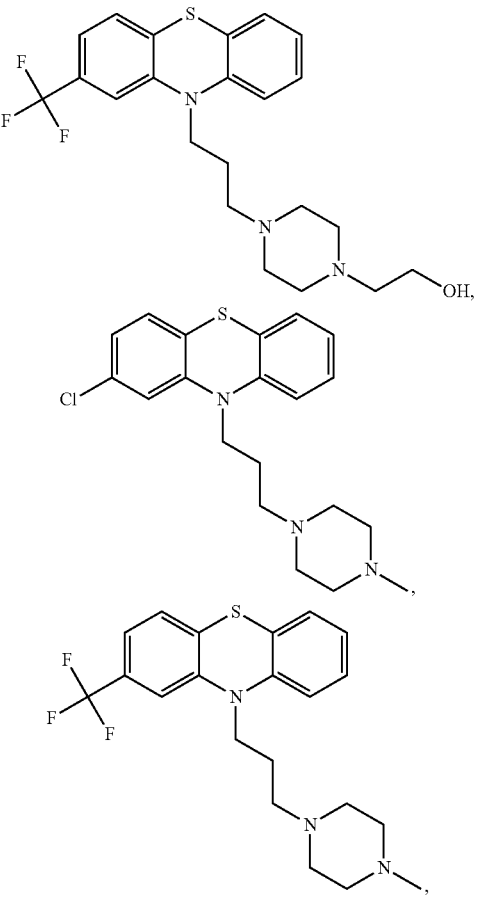

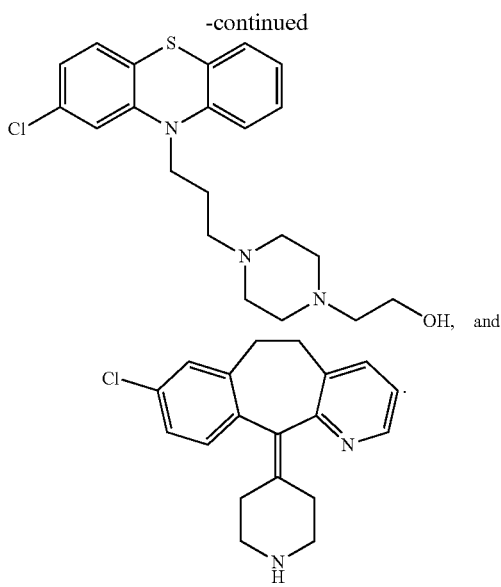

(ii) Vasodilator

In one aspect, the compositions detailed herein include a compound comprising a vasodilator. The vasodilator compounds useful in the present disclosure include the drug class of calcium channel blockers. Calcium channel blockers (CCB), calcium channel antagonists or calcium antagonists are a group of drugs that disrupt the movement of calcium (Ca2+) through calcium channels. Calcium channel blockers are used as antihypertensive drugs, i.e., as medications to decrease blood pressure in patients with hypertension. CCBs are particularly effective against large vessel stiffness, one of the common causes of elevated systolic blood pressure in elderly patients. Calcium channel blockers are also frequently used to alter heart rate (especially from atrial fibrillation), to prevent peripheral and cerebral vasospasm, and to reduce chest pain caused by angina pectoris.

N-type, L-type, and T-type voltage-dependent calcium channels are present in the zona glomerulosa of the human adrenal gland, and CCBs can directly influence the biosynthesis of aldosterone in adrenocortical cells, with consequent impact on the clinical treatment of hypertension with these agents. CCBs have been shown to be slightly more effective than beta blockers at lowering cardiovascular mortality, but they are associated with more side effects. Potential major risks however were mainly found to be associated with short-acting CCBs.

Dihydropyridine (DHP) calcium channel blockers are derived from the molecule dihydropyridine and often used to reduce systemic vascular resistance and arterial pressure. The isolation and synthesis of various vasodilator compounds is known in the art and the compounds are also manufactured commercially.

Example of vasodilator drugs include: without being limited thereto, dihydropyridine class of compounds. Specific examples are amlodipine and nilvadipine. Other non-limiting examples include aranidipine, azelnidipine, barnidipine, benidipine, cilnidipine, clevidipine, efonidipine, felodipine, isradipine, lacidipine, lercanidipine, manidipine, nicardipine, nifedipine, nimodipine, nisoldipine, nitrendipine, pranidipine.

In exemplary embodiments, a compound of the disclosure comprises a vasodilator as shown below:

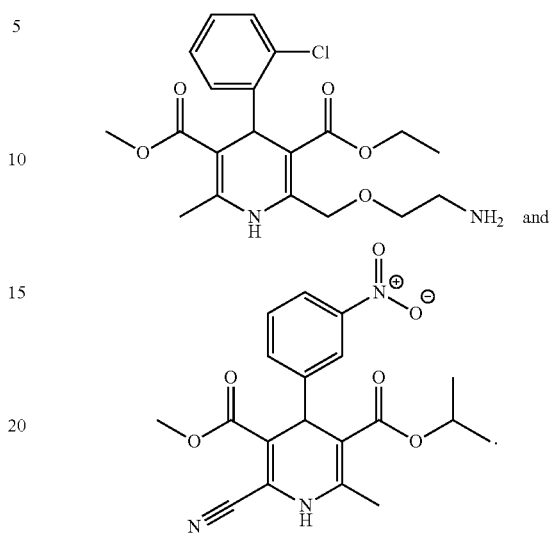

(iii) Antibiotic/Antiseptic

In one aspect, the compositions detailed herein include a compound comprising an antibiotic/antiseptic. The antibiotic/antiseptic compounds useful in the present disclosure include but are not limited to β-amino alcohols, amphipathic bisbiguanide antiseptics, cationic antiseptics, cationic polybiguanides (bisbiguanide) and gold thiolates.

In one aspect, the compositions detailed herein include a compound comprising a β-amino alcohol. Amino alcohols contain both an amine and an alcohol group. Amino alcohol derivatives have been employed as catalysts as well as coupling partners in the synthesis of many compounds. Enantiomerically pure β-amino alcohols play an increasingly important role in pharmaceutical therapy and as chiral auxiliaries in organic synthesis. Amino alcohol derivatives are currently being studied for their antimicrobial and antifungal activities, and in the modulation of the physiochemical properties of drug molecules. The amino alcohol group is present in several antibiotics, such as ethambutol for the treatment of tuberculosis. 1,2-Additions, ring-closure reactions, conjugate additions, and α-functionalization of carbonyl compounds are efficiently accomplished by β-amino alcohols as catalysts. The ready availability of β-amino alcohols from a chiral pool (e.g., L-amino acids) makes them an appealing class of versatile promoters to exploit in modern organic synthesis.

Non-limiting examples of β-amino alcohols include 2-(octylamino)-1-(4-propan-2-ylsulfanylphenyl)propan-1-ol (also known as suloctidil), 1-(3-Methyl-4-methylthiophenyl)-n-octylaminoethanol, 1-(3-Methyl-4-methylsulfanylphenyl)-2-(propan-2-ylamino)ethanol, (1S,2R)-2-(Octylamino)-1-(4-propan-2-ylsulfanylphenyl)propan-1-ol, 4-[Isopropylthio]-alpha-[1-(octylamino)ethyl]benzyl alcohol hydrochloride, Benzenemethanol, alpha-(1-(butylamino)ethyl)-4-((1-methylethyl)thio)-, hydrochloride, Benzenemethanol, 4-((1-methylethyl)thio)-alpha-(1-((1-methylpropyl)amino)ethyl)-, hydrochloride, Benzenemethanol, 4-(methylthio)-alpha-(1-(octylamino) ethyl)-, hydrochloride, 1-(4-Methylsulfanylphenyl)-2-(octylamino)propan-1-ol, Benzenemethanol, alpha-(1-(butylamino)ethyl)-4-(ethylthio)-, hydrochloride, Benzenemethanol, 4-(cyclohexylthio)-alpha-(1-(octylamino)ethyl)-, hydrochloride, 1-(4-Cyclohexylsulfanylphenyl)-2-(octylamino)propan-1-ol, Benzenemethanol, alpha-(1-(butylamino)propyl)-4-(methylthio)-, hydrochloride, Benzenemethanol, 4-(methylthio)-alpha-(1-(octylamino) propyl)-, hydrochloride, 1-(4-Methylsulfanylphenyl)-2-(octylamino)butan-1-ol, Benzenemethanol, alpha-(1-(butylamino)propyl)-4-(ethylthio)-, hydrochloride, Benzenemethanol, 4-(ethylthio)-alpha-(1-(octylamino)propyl)-, hydrochloride, Benzenemethanol, alpha-(1-((1-methylethyl)amino)ethyl)-4-((2-methylpropyl)thio)-, hydrochloride, Benzyl alcohol, alpha-(1-(butylamino)ethyl)-4-isobutylthio-, alpha-(1-(Hexylamino)ethyl)-4-((1-methylethyl)thio)benzenemethanol, 2-Propanol, 1-[[(3-chlorophenyl)methyl]amino]-3-[(4-chlorophenyl)thio]-, hydrochloride, 2-Propanol, 1-[[(3-chlorophenyl)methyl] amino]-3-[(4-chlorophenyl)thio]-, 2-Propanol, 1-[[(4-chlorophenyl)methyl]amino]-3-(phenylthio)-, 2-Propanol, 1-[[(3,4-dichlorophenyl) methyl]amino]-3-(phenylthio)-, 2-Propanol, 1-[[(4-chlorophenyl)methyl]amino]-3-[(4-methylphenyl)thio]-, hydrochloride, 2-Propanol, 1-[[(4-chlorophenyl)methyl]amino]-3-[(4-methylphenyl)thio]-, 2-Propanol, 1-[[(3-chlorophenyl)methyl]amino]-3-[(4-chlorophenyl) thio]-2-methyl-, 2-Propanol, 1-[[(3-chlorophenyl) methyl]amino]-3-[(4-chlorophenyl)thio]-2-methyl-, hydrochloride, 2-Propanol, 1-[(4-chlorophenyl)thio]-3-[methyl (phenylmethyl) amino]-, Benzenemethanamine, 3-chloro-α-[(phenylthio)methyl]-N-propyl-, and 2-Propanol, 1-[[(4-chlorophenyl)methyl]amino]-3-[(3-chlorophenyl)thio]-.

In one aspect, the compositions detailed herein include a compound comprising an amphipathic bisbiguanide antiseptic. Non-limiting examples of amphipathic bisbiguanide antiseptics include alexidine, 1-[N'-[6-[[amino-[[N'-[(2S)-2-ethylhexyl]carbamimidoyl]amino]methylidene]amino] hexyl]carbamimidoyl]-2-[(2S)-2-ethylhexyl]guanidine, 1-[N'-[6-[[amino-[[N'-(2-ethylhexyl)carbamimidoyl]amino] methylidene]amino]hexyl]carbamimidoyl]-2-(2-ethylhexyl) guanidine; dihydrofluoride, 1-(diaminomethylene)-2-(2-ethylhexyl)guanidine; hexane, 1-[N'-[6-[[amino-[[N'-(6-methylheptan-2-yl)carbamimidoyl]amino]methylidene] amino]hexyl]carbamimidoyl]-2-(6-methylheptan-2-yl) guanidine, 1-[N'-[6-[[amino-[[N'-(5-methylhexan-2-yl) carbamimidoyl]amino]methylidene]amino]hexyl] carbamimidoyl]-2-(5-methylhexan-2-yl)guanidine, 1-(N'-butylcarbamimidoyl)-2-(2-ethylhexyl)guanidine, N—[N'-[6-[[amino-[[N'-(2-ethylhexyl)carbamimidoyl]amino] methylidene]amino]hexyl]carbamimidoyl]-N'-(2-ethylhexyl)methanimidamide, and 1-[N'-[6-[[amino-[[N'-(2-ethylhexyl)carbamimidoyl]amino]methylidene]amino] hexyl]carbamimidoyl]-2-[(2R)-2-ethylhexyl]guanidine.

In one aspect, the compositions detailed herein include a compound comprising a cationic antiseptic. Non-limiting examples of cationic antiseptics include hexetidine, 1,3-Bis [(2S)-2-ethylhexyl]-5-methyl-1,3-diazinan-5-amine, 1-[(2R)-2-Ethylhexyl]-3-[(2S)-2-ethylhexyl]-5-methyl-1,3-diazinan-5-amine, 1,3-bis(2-ethylhexyl)-1,3-diazinan-5-amine, 1,3-bis(2-ethylhexyl)-1-methyl-1,3-diazinan-1-ium-5-amine, 5-methyl-1,3-bis(2-methylhexyl)-1,3-diazinan-5-amine, 2-(2-ethylhexyl)-5-methyl-1,3-diazinan-5-amine, 2,2-bis(2-ethylhexyl)-5-methyl-1,3-diazinan-5-amine, 1,3-bis(2-ethylhexyl)-N-methyl-1,3-diazinan-5-amine, 1,3-bis (2-ethylhexyl)-2,5-dimethyl-1,3-diazinan-5-amine, 1,3-bis (2-ethylhexyl)-5-methyl-1,3-diazinan-5-amine; hydrofluoride, 1,1-bis(2-ethylhexyl)-5-methyl-1,3-diazinan-1-ium-5-amine, and 1-(2-ethylhexyl)-5-methyl-3-(2-methylhexyl)-1,3-diazinan-5-amine.

In one aspect, the compositions detailed herein include a compound comprising a cationic polybiguanide. Non-limiting examples of cationic polybiguanides include chlorhexidine, 2-[6-[[amino-[[amino-(4-chloroanilino)methylidene] amino]methylidene]amino]hexyl]-1-[amino-(4-chloroanilino)methylidene]guanidine, 2-N-(4-Chlorophenyl)-4,4-dimethyl-1H-1,3,5-triazine-2,6-diamine, (1Z)-2-[6-[[amino-[(Z)-[amino-(4-chloroanilino)methylidene]amino]methylidene]amino]hexyl]-1-[amino-(4-chloroanilino)methylidene]guanidine, (1E)-2-[6-[[amino-[(Z)-[amino-(4-chloroanilino)methylidene]amino]methylidene] amino]hexyl]-1-[amino-(4-chloroanilino)methylidene] guanidine, 2-[6-[[amino-(4-chloroanilino)methylidene] amino]hexyl]-1-(4-chlorophenyl)guanidine, 1-[6-(N-carbamimidoyl-4-chloroanilino)hexyl]-1-(4-chlorophenyl) guanidine, 2-[6-[[amino-[[amino-(4-chloroanilino)methyl] amino]methylidene]amino]hexyl]-1-[amino-(4-chloroanilino)methyl]guanidine, N'-[6-[[amino-[[amino-(4-chloroanilino)methyl]amino]methyl]amino]hexyl]-N''-[amino-(4-chloroanilino)methyl]methanetriamine, and N'—[N'-[6-[[amino-[(4-chloroanilino)methylideneamino] methylidene]amino]hexyl]carbamimidoyl]-N-(4-chlorophenyl)methanimidamide.

In one aspect, the compositions detailed herein include a compound comprising a gold thiolate. Non-limiting examples of gold thiolates include auranofin, ethoxy(diethyl)phosphane; gold(1+); 3,4,5-triacetyloxy-6-(acetyloxymethyl)oxane-2-thiolate, and gold; 3,4,5-triacetyloxy-6-(acetyloxymethyl)oxane-2-thiolate; triethylphosphanium.

In exemplary embodiments, a compound of the disclosure comprises an antibiotic/antiseptic as shown below:

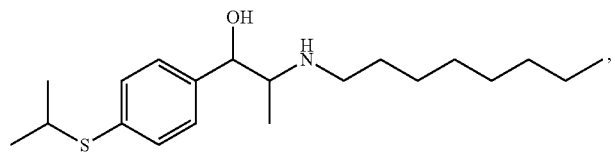, 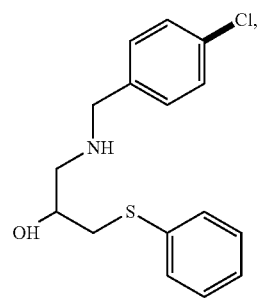

(RDR 03172)

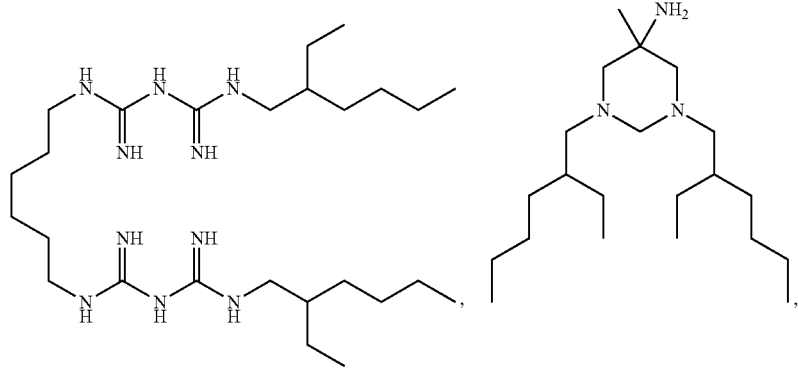

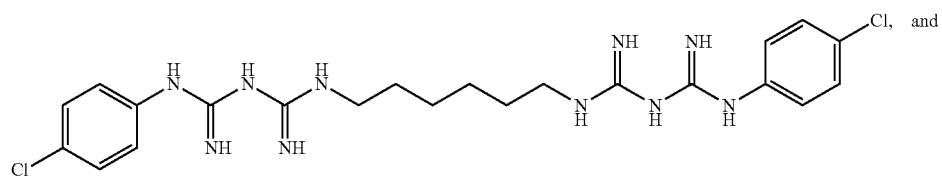

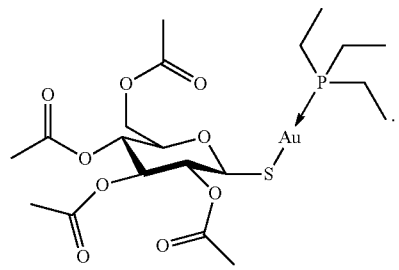

(iv) Aryl Piperazine

In one aspect, the compositions detailed herein include a compound comprising an aryl piperazine. Non-limiting examples of aryl piperazines include Piperazine, 1-(3-chlorophenyl)-4-[3-[[5-(trifluoromethyl)-2-pyridinyl]thio]propyl]-(AW 00794), Piperazine, 1-[3-(2-pyridinylthio)propyl]-4-[3-(trifluoromethyl)phenyl]-, Piperazine, 1-[3-(trifluoromethyl)phenyl]-4-[3-[[5-(trifluoromethyl)-2-pyridinyl]thio]propyl]-, Piperazine, 1-[5-(2-pyridinylthio)pentyl]-4-[3-(trifluoromethyl)phenyl]-, Piperazine, 1-[3-(4-pyridinylthio)propyl]-4-[3-(trifluoromethyl)phenyl]-, 2(1H)-Pyridinone, 6-[[3-[4-[3-(trifluoromethyl)phenyl]-1-piperazinyl]propyl]thio]-, Piperazine, 1-(3-chlorophenyl)-4-[3-(2-pyridinylthio)propyl]-, 3-Pyridinol, 2-[[3-[4-[3-(trifluoromethyl)phenyl]-1-piperazinyl]propyl]thio]-, Pyrimidine, 4-[[3-[4-[3-(trifluoromethyl)phenyl]-1-piperazinyl]propyl]thio]-, Piperazine, 1-[3-[(4-fluorophenyl)thio]propyl]-4-[3-(trifluoromethyl)phenyl]-, Quinoline, 2-[[3-[4-(3-chlorophenyl)-1-piperazinyl]propyl]thio]-, 3-Pyridinecarbonitrile, 2-[[3-[4-(3-chlorophenyl)-1-piperazinyl]propyl]thio]-6-methyl-4-(trifluoromethyl)-, Piperazine, 1-[3-[(5-chloro-2-pyridinyl)oxy]propyl]-4-[3-(trifluoromethyl)phenyl]-, Piperazine, 1-[3-[(4-fluorophenyl)thio]propyl]-4-[4-(trifluoromethyl)phenyl]-, and Piperazine, 1-[3-[(4-fluorophenyl)thio]propyl]-4-[4-(trifluoromethyl)phenyl]-, hydrochloride (1:1).

In an exemplary embodiment, a compound of the disclosure comprises an aryl piperazine as shown below:

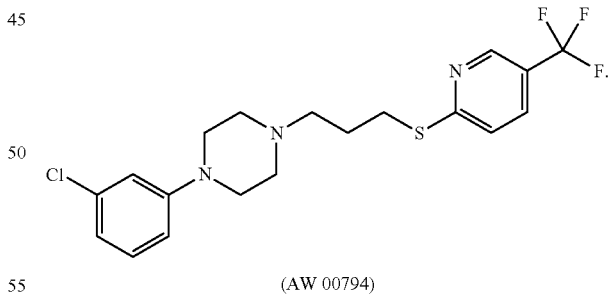

(AW 00794)

(v) Antidepressant

In one aspect, the compositions detailed herein include a compound comprising an antidepressant. Non-limiting examples of suitable antidepressants include aprepitant, sertraline, 4-(3,4-Dichlorophenyl)-n-methyl-1,2,3,4-tetrahydronaphthalen-1-amine, (1R,4R)-4-(3,4-Dichlorophenyl)-N-methyl-1,2,3,4-tetrahydronaphthalen-1-amine, Desmethylsertraline, (1S,4S)-4-(3,4-dichlorophenyl)-N-(111C) methyl-1,2,3,4-tetrahydronaphthalen-1-amine, N-[4-(3,4-dichlorophenyl)-1,2,3,4-tetrahydronaphthalen-1-yl]

acetamide, 4-(3,4-dichlorophenyl)-1,2,3,4-tetrahydronaphthalen-1-amine, (1S,4R)-4-(3,4-Dichlorophenyl)-N-methyl-1,2,3,4-tetrahydronaphthalen-1-amine, methyl N—[(Z)-[1-amino-2-[2-[1-[3,5-bis(trifluoromethyl)phenyl]ethoxy]-3-(4-fluorophenyl)morpholin-4-yl]ethylidene]amino]carbamate, methyl N—[(Z)-[1-amino-2-[(2R,3S)-2-[(1R)-1-[3,5-bis(trifluoromethyl)phenyl]ethoxy]-3-(4-fluorophenyl)morpholin-4-yl]ethylidene]amino]carbamate, [3-[[(2R,3S)-2-[(1R)-1-[3,5-bis(trifluoromethyl)phenyl]ethoxy]-3-(4-fluorophenyl)morpholin-4-yl]methyl]-5-oxo-1H-1,2,4-triazol-4-yl] phosphonic acid, 1-[3-[[2-[[3,5-bis(trifluoromethyl)phenyl]methoxy]-3-phenylmorpholin-4-yl]methyl]-5-oxo-1H-1,2,4-triazol-4-yl]ethyl ethyl carbonate, and [3-[[2-[1-[3,5-bis(trifluoromethyl)phenyl]ethoxy]-3-(4-fluorophenyl)morpholin-4-yl]methyl]-5-oxo-1H-1,2,4-triazol-4-yl] phosphonic acid.

In an exemplary embodiment, a compound of the disclosure comprises an antidepressant as shown below:

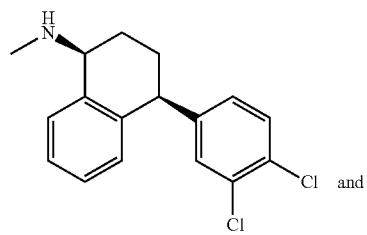

and

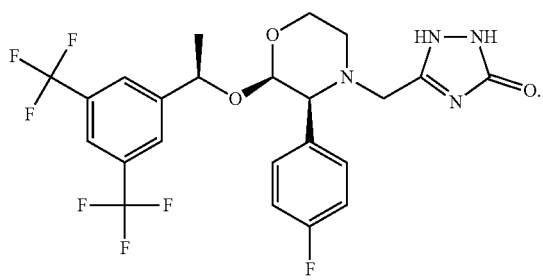

(vi) Chemotherapeutic

In one aspect, the compositions detailed herein include a compound comprising a chemotherapeutic. Non-limiting examples of suitable chemotherapeutics include toremifene, perhexiline, clomifene, 2-[4-(1,2-Diphenylbut-1-enyl)phenoxy]-N,N-dimethylethanamine, 2-[4-(4-Chloro-1,2-diphenylbut-1-enyl)phenoxy]-N,N-dimethylethanamine, 2-[4-(1,2-Diphenylbut-1-enyl)phenoxy]ethyl-trimethylazanium, 2-[4-(1,2-diphenylbut-1-enyl)phenoxy]-N,N-dimethylethanamine oxide, 4-Pentan-2-yl-N-(4-pentan-2-ylcyclohexyl)cyclohexan-1-amine, (2S)-2-(2,2-Dicyclohexylethyl)piperidine, N-Dicyclohexylmethylpiperazine, 4-propan-2-yl-N-(4-propan-2-ylcyclohexyl)cyclohexan-1-amine, and (2R)-2-(2,2-dicyclohexylethyl)piperidine.

In an exemplary embodiment, a compound of the disclosure comprises an chemotherapeutic as shown below:

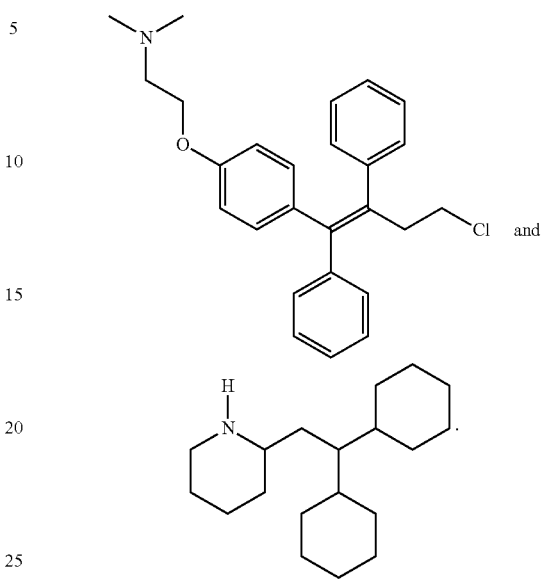

b) Components of the Composition

The present disclosure also provides pharmaceutical compositions. The pharmaceutical composition comprises one or more proteotoxicity reducing agent or derivatives thereof, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional drug or therapeutically active agent in addition to the one or more of a proteotoxicity reducing agent or derivatives thereof. Thus, in addition to the therapies described herein, one may also provide to the subject other therapies known to be efficacious for treatment of the disease, disorder, or condition. In some embodiments, the additional drug or therapeutic agent maybe a small molecule, a polypeptide, a nucleic acid, a cell or cell lysate, a virus (e.g. gene therapy), an antibody or the like. In some embodiments, the administration of one or more of a proteotoxicity reducing agent or derivatives thereof maybe administered before or after surgery. In some embodiments, the secondary agent is selected from a corticosteroid, a non-steroidal anti-inflammatory drug (NSAID), an intravenous immunoglobulin, a kinase inhibitor, a fusion or recombinant protein, a monoclonal antibody, or a combination thereof. In some embodiments, agents suitable for combination therapy include but are not limited to inhaled bronchodilators and inhaled steroids. In some embodiments, suitable combinational therapy incudes augmentation therapy, for example, the use of alpha-1 antitrypsin protein (AAT) from the plasma of healthy human donors is used to increase the alpha-1 levels circulating in the blood and lungs of Alphas diagnosed with emphysema. In some embodiments, agents suitable for combination therapy include but are not limited to antioxidants and/vitamins. In some embodiments, agents suitable for combination therapy include but are not limited to cholinesterase inhibitors. In some embodiments, suitable cholinesterase inhibitors include donepezil, galantamine and rivastigmine. In some embodiments, agents suitable for combination therapy include but are not limited to memantine or antidepressants. In some embodiments, agents suitable for combination therapy include but are not limited to carbidopa-levodopa, carbidopa-levodopa infusion, dopamine agonists, MAO B inhibitors, catechol O-methyltransferase (COMT) inhibitors, anticholinergics, or amantadine. In some embodiments, agents suitable for combination therapy include rilzule or tetrabenazine.

In some embodiments, the additional drug or therapeutically active agent induces anti-inflammatory effects. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, curcumin, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, lysofylline, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, mepolizumab, prodrugs thereof, and a combination thereof.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

(d) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intraocular, intradermal, intravenous, intramuscular, intraarticular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising the one or more of a proteotoxicity reducing agent or derivatives thereof, is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the one or more of a proteotoxicity reducing agent or derivatives thereof, in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the one or more of a proteotoxicity reducing agent or derivatives thereof may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3, 3, 3',3'-tetramethylindo carbocyanine methanesulfonate, N-4-(delinoleylaminostyryl)-N- methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the one or more of a tricyclic antipsychotic, vasodilator, antibiotic/antiseptic, aryl piperazine or derivatives thereof, may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of one or more of a proteotoxicity reducing agent or derivatives thereof, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The one or more of a tricyclic antipsychotic, vasodilator, antibiotic/antiseptic, aryl piperazine or derivatives thereof may be encapsulated in a microemulsion by any method generally known in the art.

In yet another embodiment, one or more of a proteotoxicity reducing agent or derivatives thereof, may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

Generally, a safe and effective amount one or more of a proteotoxicity reducing agent or derivatives thereof is, for example, that amount that would cause the desired therapeutic effect in a subject while minimizing undesired side effects. In various embodiments, an effective amount of one or more of a proteotoxicity reducing agent or derivatives thereof described herein can substantially reduce proteotoxicity in a subject suffering from a proteopathy. In some embodiments, an effective amount is an amount capable of treating a proteinopathies, such as, Alpha-1-antitrypsin deficiency, Non-alcoholic fatty liver disease, Alzheimer's disease, Parkinson's disease, Amyotrophic Lateral Sclerosis, and Huntington's disease. In some embodiments, an effective amount is an amount capable of correcting cell and/or organ dysfunction caused by protein aggregation/accumulation. In some embodiments, an effective amount is an amount capable of reducing misfolded or mutant protein accumulation in a target organ. In some embodiments, an effective amount is an amount capable of enhancing clearance of a misfolded or mutant protein from a target organ or cell. In some embodiments, an effective amount is an amount capable of enhancing autophagy in a cell or subject in need thereof.

When used in the treatments described herein, a therapeutically effective amount of one or more of a proteotoxicity reducing agent or derivatives thereof can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to modulate proteopathy diseases and disorders.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Dosages of the pharmaceutical compositions can vary between wide limits, depending upon the disease or disorder to be treated, the age and condition of the subject to be treated. In an embodiment a proteotoxicity reducing agent is contacted with a sample the dose may be at a concentration of about 0.01 µM to about 10 µM. For example, the concentration of a proteotoxicity reducing agent may be about 0.01, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9 or about 10 µM. Additionally, the concentration of a proteotoxicity reducing agent may be greater than 10 µM. For example, the concentration of a proteotoxicity reducing agent may be about 10, about 15, about 20, about 25, about 30, about 35, about 40, about 45, about 50, about 55, about 60, about 65, about 70, about 75, about 80, about 85, about 90, about 95 or about 100 µM.

In an embodiment where the composition comprising one or more of a proteotoxicity reducing agent is administered to a subject, the dose may be from about 0.1 mg/kg to about 500 mg/kg. For example, the dose of a proteotoxicity reducing agent may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of a proteotoxicity reducing agent may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of a proteotoxicity reducing agent may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg. In a specific embodiment, the dose of a proteotoxicity reducing agent may be about 50 mg/kg. The composition comprising one or more of a proteotoxicity reducing agent may be administered to a subject at various frequencies, intervals and durations by various routes (topical application, enteral, or parenteral administration).

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of one or more of a proteotoxicity reducing agent or derivatives thereof can occur as a single event or over a time course of treatment. For example, one or more of a proteotoxicity reducing agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a proteopathy (e.g. Alpha-1-antitrypsin deficiency, Non-alcoholic fatty liver disease, Alzheimer's disease, Parkinson's disease, Amyotrophic Lateral Sclerosis, and Huntington's disease).

The present disclosure encompasses pharmaceutical compositions comprising compounds as disclosed above, so as to facilitate administration and promote stability of the active agent. For example, a compound of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). For the purposes of the aspects and embodiments of the invention, the subject may be a human or any other animal.

(II) Methods

The present disclosure encompasses a method of treating a proteinopathy. Proteinopathies encompasses any disease or condition caused by a malformed protein. The malformed protein may be a result of a mutation or caused by a damaged/misfolded protein or fragment thereof. In general, in most organ systems, intracellular protein homeostasis is the sum of many factors, including chromosomal state, protein synthesis, post-translational processing and transport, folding, assembly and disassembly into macromolecular complexes, protein stability and clearance. If any one of these processes is perturbed by internal or external stimuli, the cell must respond to either regulate that specific process or compensate by regulating some other function, which may not necessarily be closely linked mechanistically to the particular system (e.g., up- or down-regulation of RNA metabolism). If a protein contains a mutation that predisposes it to incorrect folding or aggregation, or some other ancillary process is disturbed such that protein misfolding or aggregation occurs, the potential for proteotoxicity arises. As used herein "proteotoxicity" refers to the adverse effects a damaged or misfolded protein exerts on a cell (e.g. a toxic effect on cellular metabolism or increased cell death).

Protein homeostasis is important to the overall health of any cell type, but the post-mitotic cell is particularly challenged if homeostasis is perturbed to the extent that misfolded proteins accumulate and aggregates begin to form. One would therefore expect that, in an organ whose essential cells are largely post-mitotic, proteotoxic processes would have a particularly significant impact on normal function. If toxic concentrations of proteotoxic proteins or aggregates are reached, the cell cannot divide and effectively, after reaching the size characteristic for its type, decrease the concentration of toxic proteins or aggregates. Compounding the sensitivity of the organ, if proteotoxicity leads to cell death, the tissue has no easy way of replacing the damaged or dead cells. As such the mechanisms dealing with protein homeostasis and quality control must be highly effective and regulated in cell types such as the neuron, hepatocyte and cardiomyocyte and when these systems are perturbed, there are significant pathogenic consequences. In fact, the brain, in which critical cell types such as the neuron are largely post-mitotic, suffers from numerous proteinopathies. For example, many neurodegenerative diseases, including Huntington's disease, Parkinson's disease, prion disease, and amyotrophic lateral sclerosis are characterized by the accumulation of significant protein aggregates and a number of pathogenic consequences can be traced to malfunctions in either the chaperones themselves or in the clearance machinery that functions to remove misfolded or damaged proteins. In the liver, al-antitrypsin deficiency (ATD) is characterized by a point mutation that leads to misfolding of mutant alpha-1-antitrypsin Z (ATZ). ATZ accumulates in the endoplasmic reticulum (ER) of cells in which it is synthesized with reduced secretion such that serum levels are only 10-15% of normal. Because liver is the predominant site of AT synthesis, accumulation of mutant ATZ within the ER of hepatocytes leads to proteotoxic consequences, including hepatic fibrosis/cirrhosis and carcinogenesis, by gain-of-function. In the heart, the expression of ectopic polypeptides capable of exerting proteotoxic effects can, by themselves, cause cardiac disease and heart failure, even when present in only small amounts.

Generally, the methods as described herein comprise administration of a therapeutically effective amount of one or more of a proteotoxicity reducing agent or derivatives thereof so as to substantially reduce proteotoxicity in a cell or subject suffering from a proteinopathy. In one aspect, the present disclosure encompasses a method of treating a proteinopathies, such as, Alpha-1-antitrypsin deficiency, Non-alcoholic fatty liver disease, Alzheimer's disease, Parkinson's disease, Amyotrophic Lateral Sclerosis, and Huntington's disease. In another aspect, the present disclosure encompasses a method of correcting cell and/or organ dysfunction caused by protein aggregation or accumulation. In yet another aspect, the present disclosure encompasses a method of reducing misfolded or mutant protein accumulation in a target cell or organ. In still another aspect, the present disclosure encompasses a method of enhancing clearance of a misfolded or mutant protein from a target cell or organ. In another aspect, the present disclosure encompasses a method of enhancing autophagy in a cell or subject in need thereof. In general, the methods comprise administering a composition comprising a therapeutically effective amount of one or more of a proteotoxicity reducing agent or derivatives thereof. In still yet another aspect, the present disclosure provides a composition comprising one or more of a proteotoxicity reducing agent or derivatives thereof, for use in vitro, in vivo, in situ or ex vivo. Suitable compositions comprising one or more of a proteotoxicity reducing agent or derivatives thereof are disclosed herein, for instance those described in Section I.

Disclosed herein are methods of treatment for a proteinopathy comprising administering to a subject an effective amount of a composition comprising one or more of a proteotoxicity reducing agent or derivatives thereof. The one or more of a proteotoxicity reducing agent or derivatives thereof substantially reduce proteotoxicity. In some embodiments, reduced proteotoxicity results from a reduction in accumulation of the misfolded or mutant protein relative to an untreated cell. In some embodiments, reduced proteotoxicity results from a reduction in aggregation of the misfolded or mutant protein relative to an untreated cell. A reduction in protein accumulation and/or aggregation includes in non-liming examples, a reduction in the count, size, and/or area percentage of the protein accumulation and/or aggregation retained in the cell, tissue or organism. Methods of determining protein accumulation and aggregation are known in the art. For example, these methods include various imaging techniques such as fluorescence microscopy, positron emission tomography (PET) using, e.g., florbetapir-F18 (AV-45) or Pittsburgh Compound-B-C11 (PiB) as radiotracers, flow-cytometry, solid-state NMR of whole cells, and enzymatic activity assays.

Autophagy is characterized by membranes that are committed to growth, becoming double-membrane vesicles that surround a portion of cytoplasm, organelles, glycogen and protein aggregates. In autophagy, small ubiquitin-like molecules (LC3, GABARAP, GATE 16, ATG12) are transferred from the conjugation systems to membranes for their growth and commitment to become a double-membrane vesicle, called the autophagosome. This reaction requires the recruitment and assembly of different components of the autophagy machinery on phospholipids but only the ubiquitin-like components, LC3, GABARAP and GATE16, are covalently bound to the phospholipid phosphatidylethanolamine. In the cells there are two conjugation systems that work in parallel and are composed by the Autophagy Genes (ATG) which are highly conserved between species and act in a hierarchical manner. The coordinated action of these conjugation complexes allows the commitment of the membrane to become autophagosome, the elongation of the phospholipid bilayer and fusion to form a mature double membrane vesicle that is finally docked to the lysosomes for degradation of the cargo, that is, the material that was initially engulfed by the autophagosome. The fusion of the outer membrane of the autophagosome with the lysosomal membrane also determines the degradation of the inner membrane and of the proteins that are associated with it. In some embodiments, administration of one or more of a proteotoxicity reducing agent or derivatives thereof to a subject results enhanced autophagy thereby reducing proteotoxicity. Enhancing autophagy includes, enhance and/or accelerate the intracellular autophagy process and facilitate the removal and elimination of aggregated protein globules or portions of the globules retained in cells, removing damaged organelles, and/or attenuating the apoptotic response to various forms of stress, leading to an improved treatment of the proteinopathy and prevention and treatment of conditions and diseases associated with the proteinopathy.

In some embodiments, the methods comprise administering a composition comprising, consisting essentially of, or consisting of a tricyclic antipsychotic and a vasodilator. In one aspect, the tricyclic antipsychotic is prochlorperazine and the vasodilator is amlodipine. In one aspect, the tricyclic antipsychotic is prochlorperazine and the vasodilator is nilvadipine. In one aspect, the tricyclic antipsychotic is desloratadine and the vasodilator is amlodipine.

In some embodiments, the methods comprise administering a composition comprising, consisting essentially of, or consisting of a tricyclic antipsychotic and an antibiotic/antiseptic. In one aspect, the tricyclic antipsychotic is prochlorperazine and the antibiotic/antiseptic is auranofin. In one aspect, the tricyclic antipsychotic is prochlorperazine and the antibiotic/antiseptic is alexidine. In one aspect, the tricyclic antipsychotic is prochlorperazine and the antibiotic/antiseptic is chlorhexidine. In one aspect, the tricyclic antipsychotic is prochlorperazine and the antibiotic/antiseptic is hexetidine.

In some embodiments, the methods comprise administering a composition comprising, consisting essentially of, or consisting of a tricyclic antipsychotic and an antidepressant. In one aspect, the tricyclic antipsychotic is prochlorperazine and the antidepressant is sertraline. In one aspect, the tricyclic antipsychotic is prochlorperazine and the antidepressant is apreitant.

In some embodiments, the methods comprise administering a composition comprising, consisting essentially of, or consisting of a tricyclic antipsychotic and a chemotherapeutic. In one aspect, the tricyclic antipsychotic is prochlorperazine and the chemotherapeutic is toremifene. In one aspect, the tricyclic antipsychotic is prochlorperazine and the chemotherapeutic is perhexiline.

In some embodiments, the methods comprise administering a composition comprising, consisting essentially of, or consisting of a vasodilator and a chemotherapeutic. In one aspect, the vasodilator is amlodipine and the chemotherapeutic is toremifene.

Methods described herein are generally performed on a subject in need thereof. A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

(III) Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to compositions and pharmaceutical formulations comprising one or more of a proteotoxicity reducing agent, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "μg", as used herein, is intended to mean micrograms. The term "h", as used herein, is intended to mean hour. The term "min", as used herein, is intended to mean minute. The term "M", as used herein, is intended to mean molar. The term "μL", as used herein, is intended to mean microliter. The term "μM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

The term "alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms (C.sub.1-20alkyl), suitably 1 to 10 carbon atoms (C.sub.1-10alkyl), preferably 1 to 8 carbon atoms (C.sub.1-8alkyl), more preferably 1 to 6 carbon atoms (C.sub.1-4alkyl), and even more preferably 1 to 4 carbon atoms (C.sub.1-4alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl, and the like.

The term "alkenyl" as used herein alone or as part of a group refers to monovalent hydrocarbon radicals having a straight or branched hydrocarbon chains having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl, and the like.

The term "alkynyl" as used herein alone or as part of a group refers to monovalent hydrocarbon radicals having a straight or branched hydrocarbon chains having one or more triple bonds and containing from 2 to about 10 carbon atoms, more preferably from 2 to about 5 carbon atoms. Examples of alkynyl radicals include ethynyl, propynyl, (propargyl), butynyl, and the like.

The term "aryl" as used herein, alone or as part of a group, includes an organic radical derived from an aromatic hydrocarbon by removal of one hydrogen, and includes monocyclic and polycyclic radicals, such as phenyl, biphenyl, naphthyl.

The term "alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy, and the like.

The term "cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl, and the like.

The term "cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl, and the like.

The term "substituted" as used herein means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups.

The term "unsubstituted" as used herein means that the carbon chain or ring contains no other substituents other than carbon and hydrogen.

The term "branched" as used herein means that the carbon chain is not simply a linear chain. "Unbranched" means that the carbon chain is a linear carbon chain.

The term "saturated" as used herein means that the carbon chain or ring does not contain any double or triple bonds. "Unsaturated" means that the carbon chain or ring contains at least one double bond. An unsaturated carbon chain or ring may include more than one double bond.

The term "hydrocarbon group" means a chain of 1 to 25 carbon atoms, suitably 1 to 12 carbon atoms, more suitably 1 to 10 carbon atoms, and most suitably 1 to 8 carbon atoms. Hydrocarbon groups may have a linear or branched chain structure. Suitably the hydrocarbon groups have one branch.

The term "carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, suitably 4 to 7 carbon atoms, and more suitably 5 to 6 carbon atoms in the ring. Bicyclic carbocyclic groups contain 8 to 12 carbon atoms, preferably 9 to 10 carbon atoms in the rings.

The term "heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

The terms "Isomer," "isomeric form," "stereochemically isomeric forms," or "stereolsomeric forms," as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers, and/or conformers of the basic molecular structure of said compound. More in particular, sterogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Using a C. elegans model a high-throughput drug screen was conducted to identify drug combinations that are efficacious in reversing the proteotoxicity due to a proteinopathy (FIG. 1-FIG. 4). Alpha-1-antitrypsin Deficiency (ATD) ATD was used as prototype of diseases caused by misfolded proteins. Using this approach, multiple drugs and drug combinations have been identified that have been shown to be efficacious in mammalian models. Drug combinations were confirmed to be synergistic via isobologram analyses. Some of the drugs work (at least in part) by enhancing autophagy. Autophagy is a cellular process that declines with age and is implicated in numerous diseases.

Figure 5A:
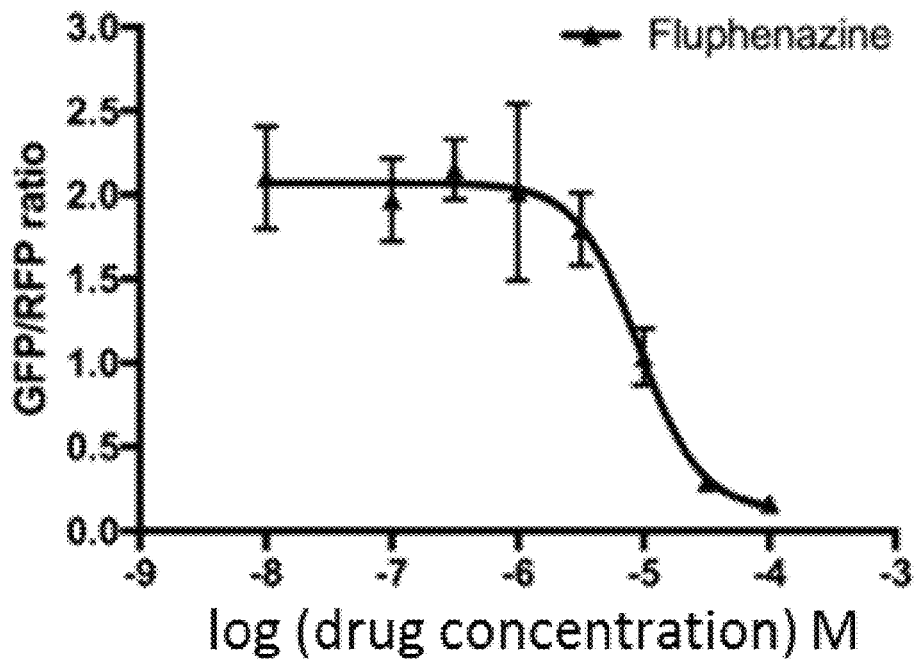
FIG. 5A, FIG. 5B, FIG. 5C, FIG. 5D, FIG. 5E and FIG. 5F show 8-point dose response curves of other phenothiazines that reduce mutant AT accumulation in a dose-dependent manner.
Figure 5B:
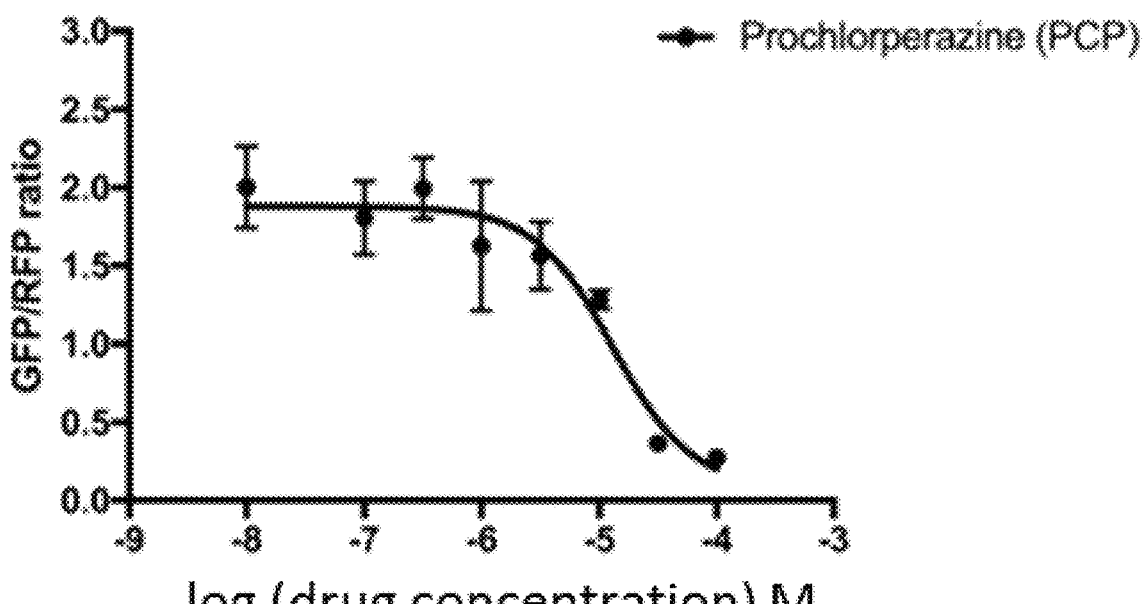
Figure 5C:
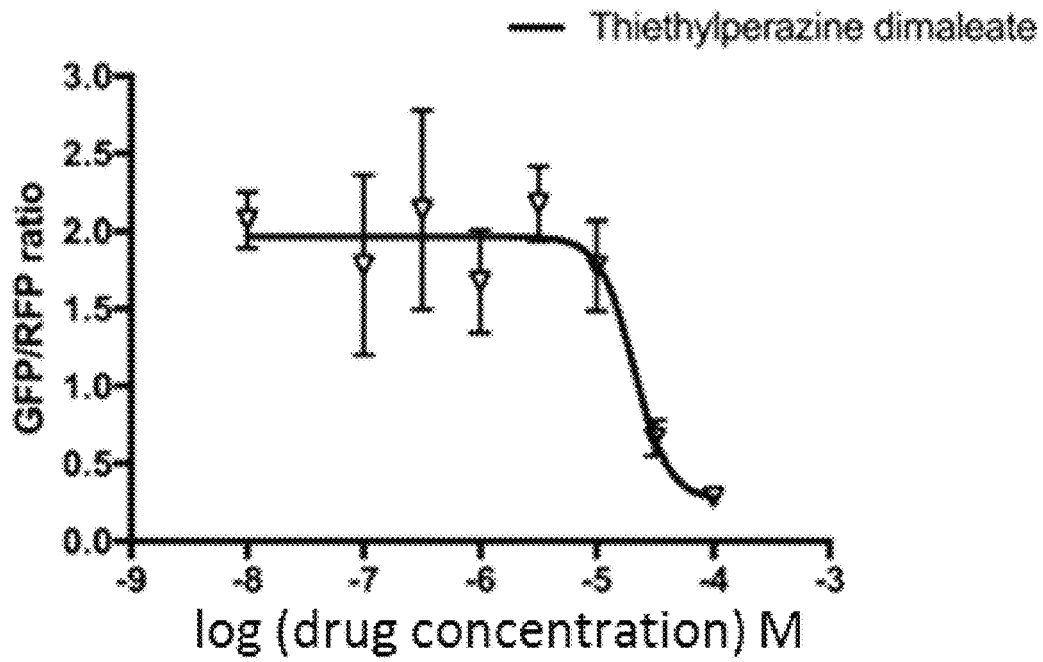
Figure 5D:
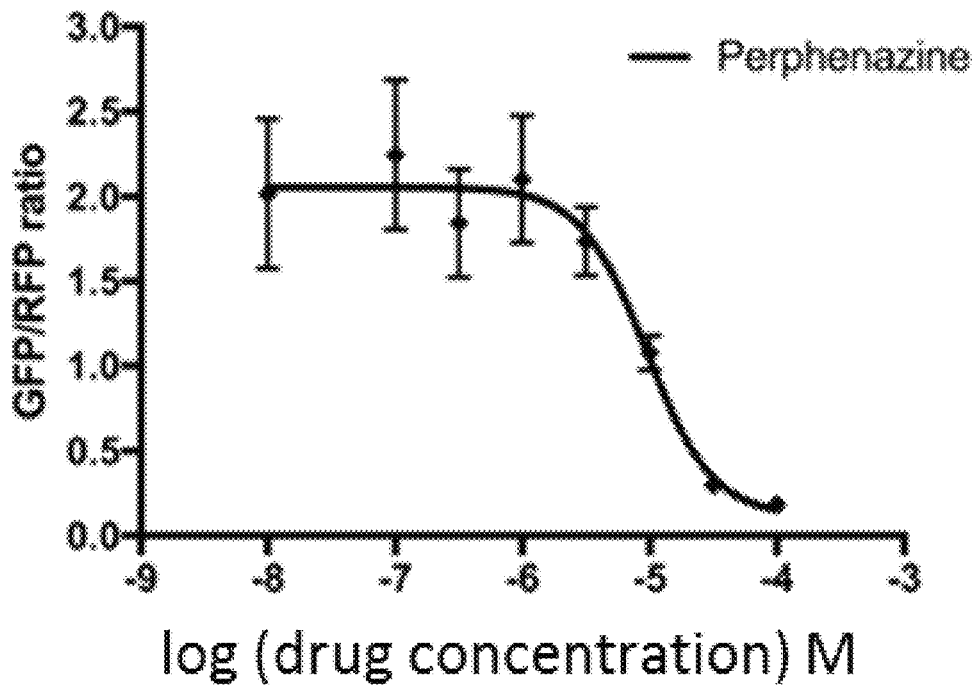
Figure 5E:
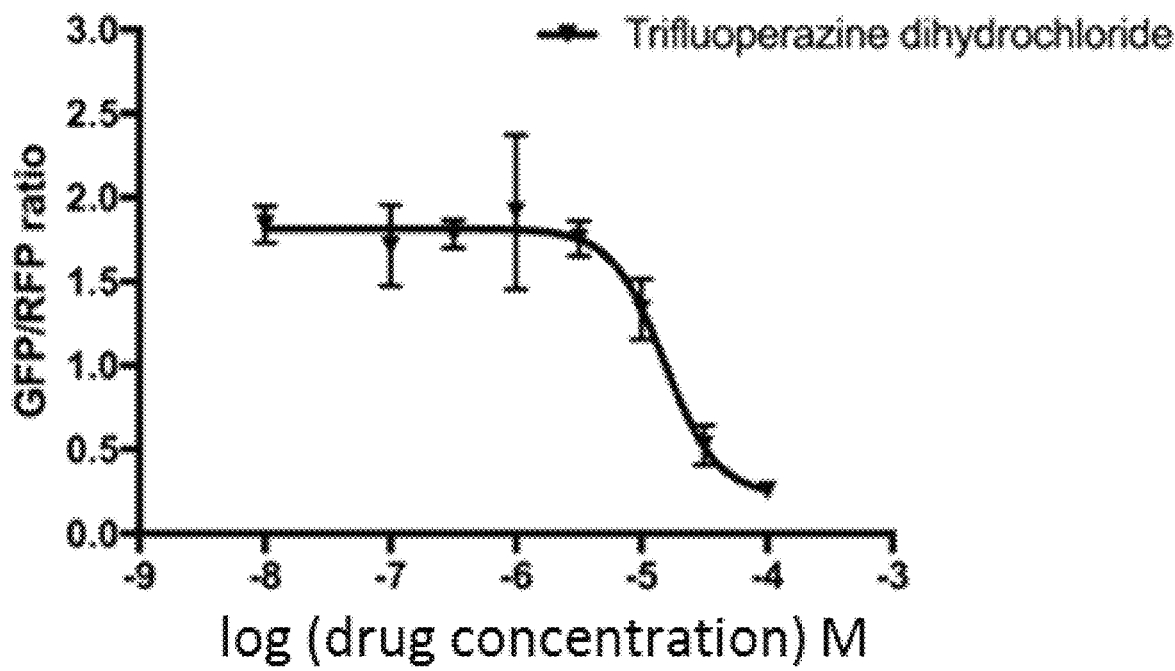
Figure 5F:
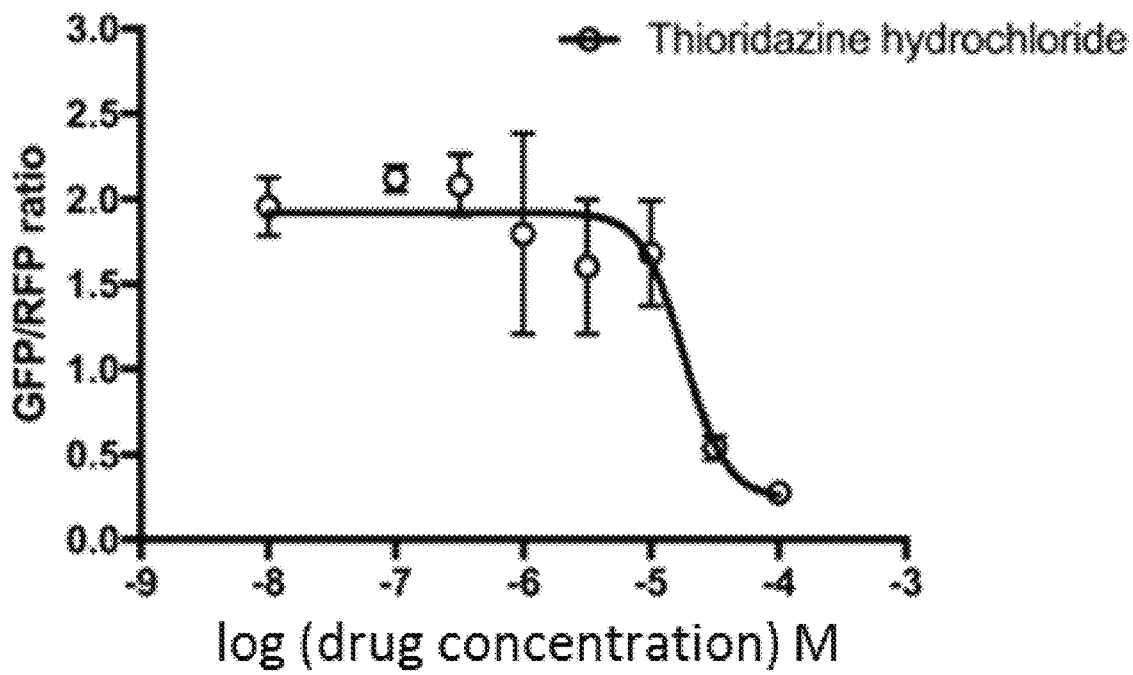
Figure 6A:
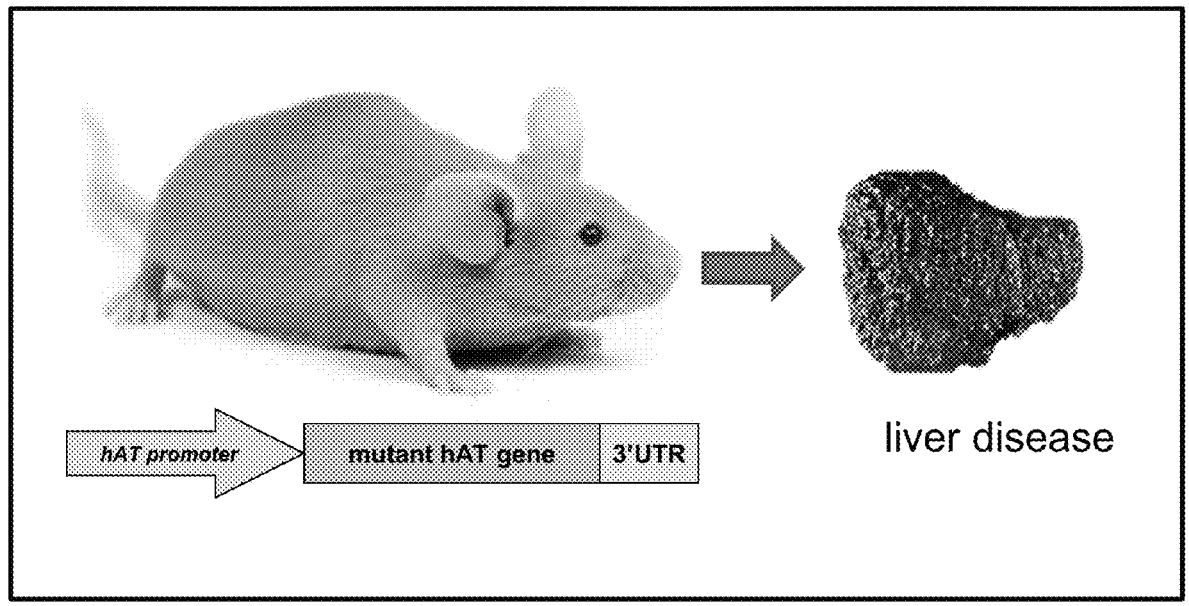
FIG. 6A, FIG. 6B, and FIG. 6C depict fluphenazine reduces mutant AT accumulation in the mouse model of ATD.
Figure 6B:
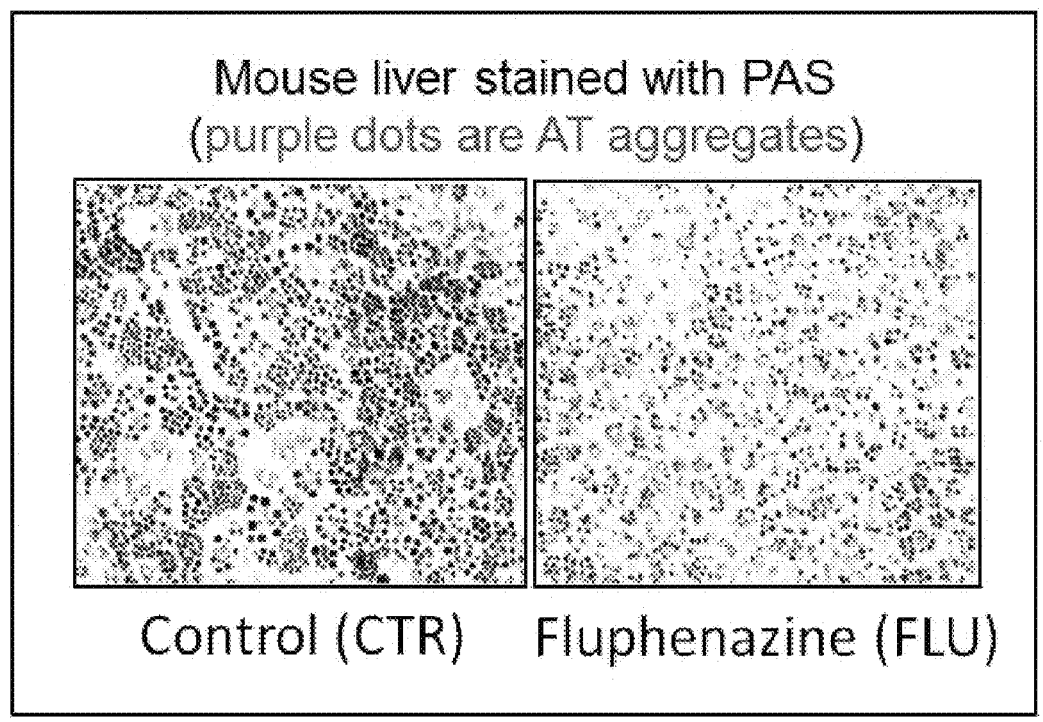
Figure 6C:
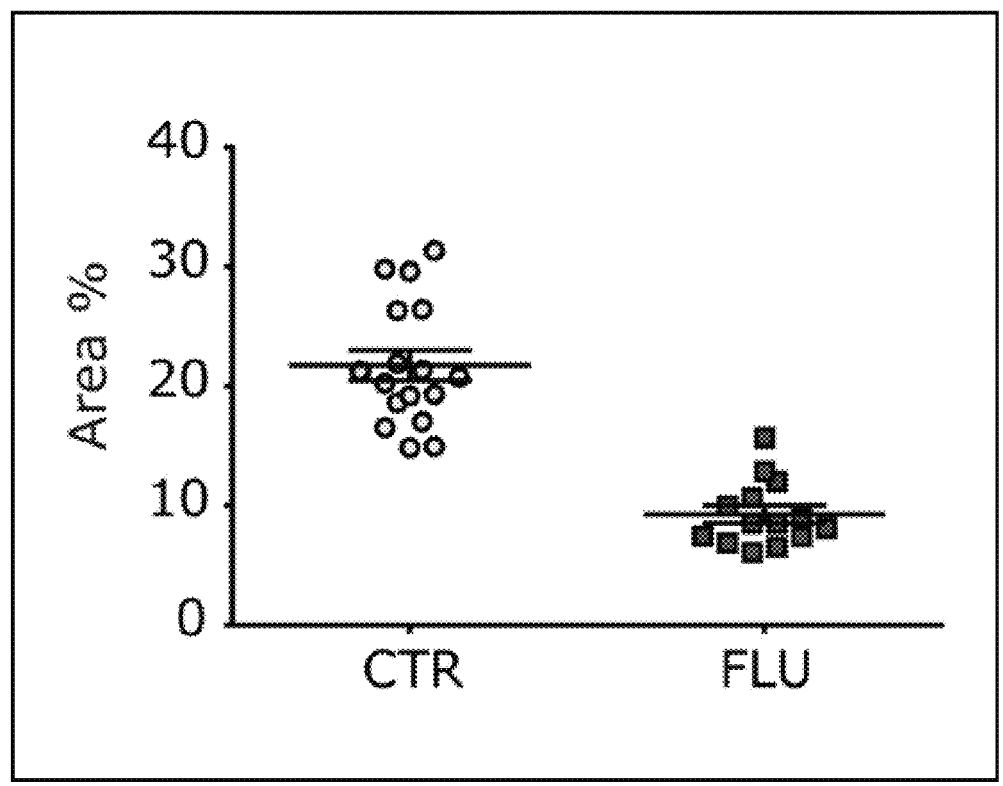
Figure 7A:
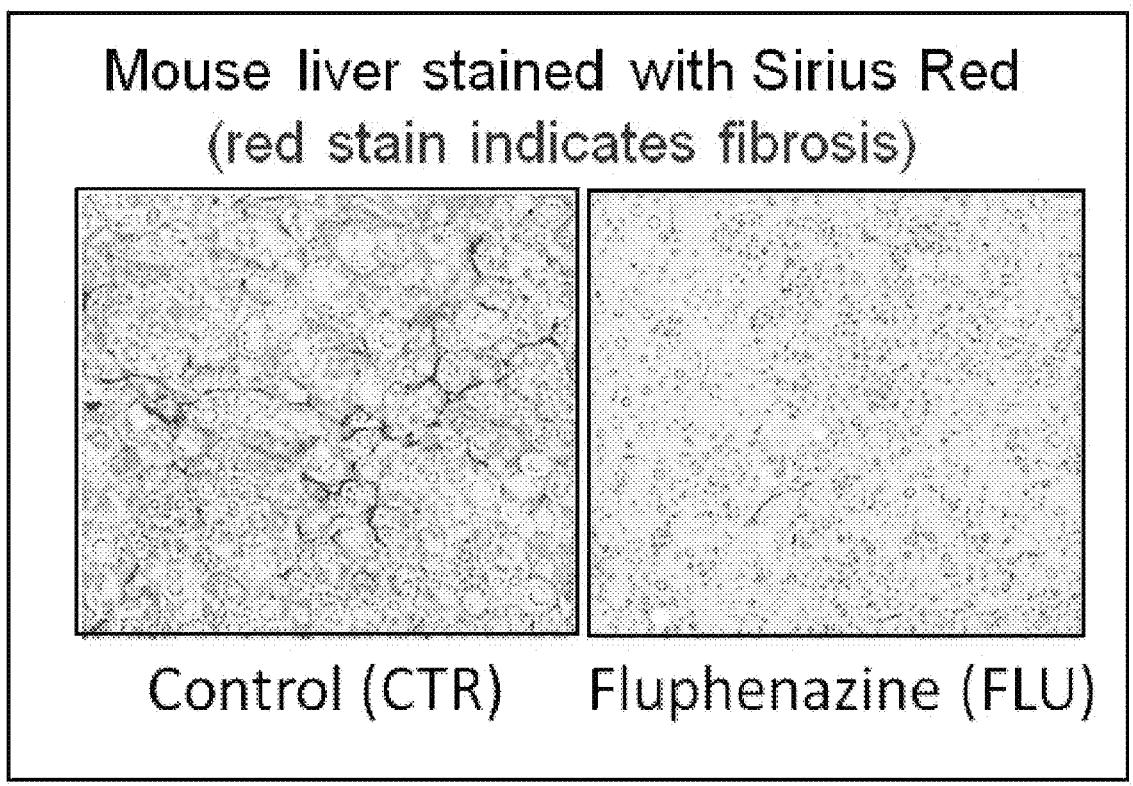
FIG. 7A and FIG. 7B shows reduction of liver injury (fibrosis) following treatment with fluphenazine.
Figure 7B:
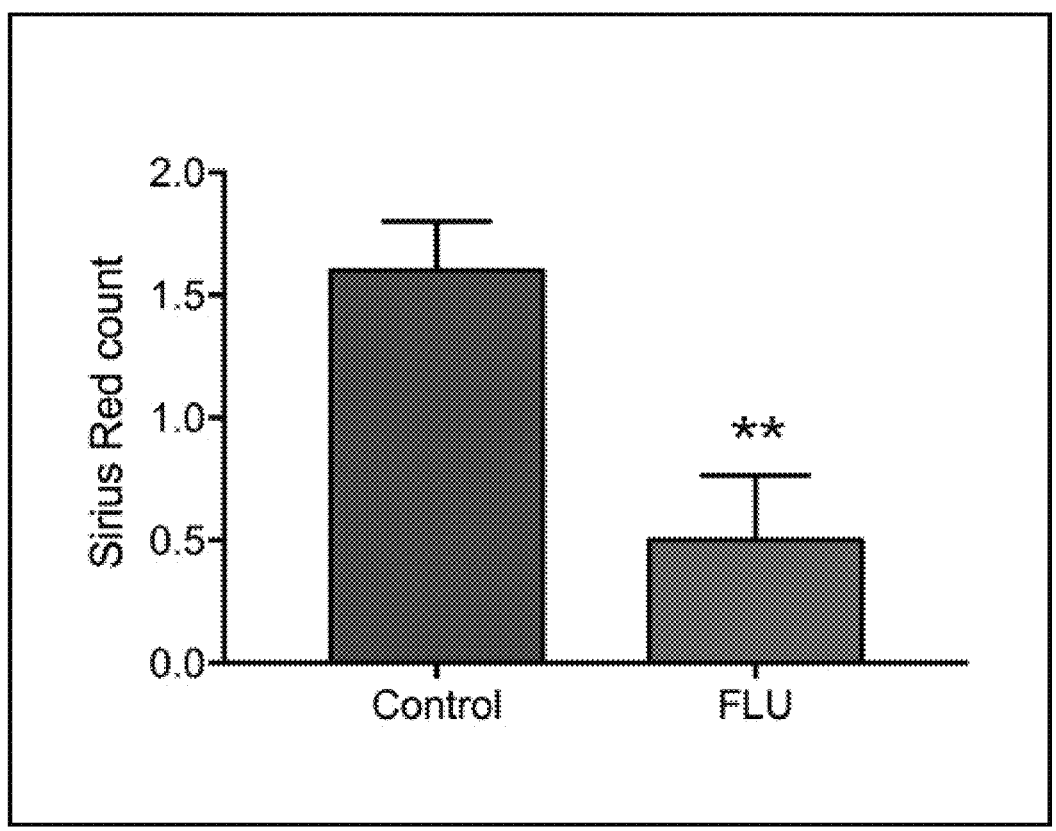
Figure 8A:
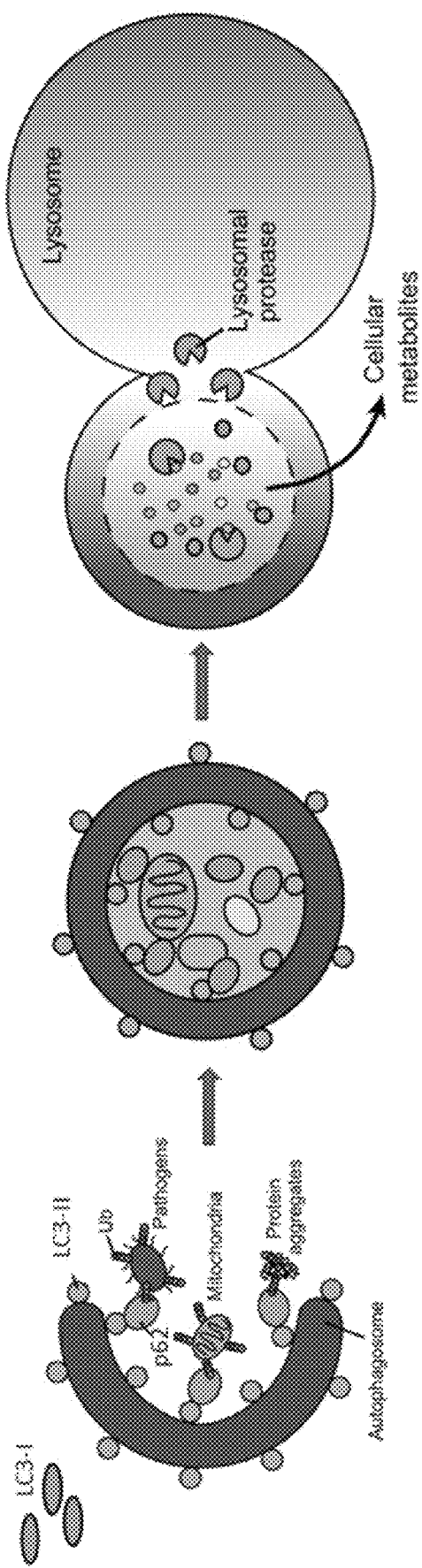
Figure 8B:
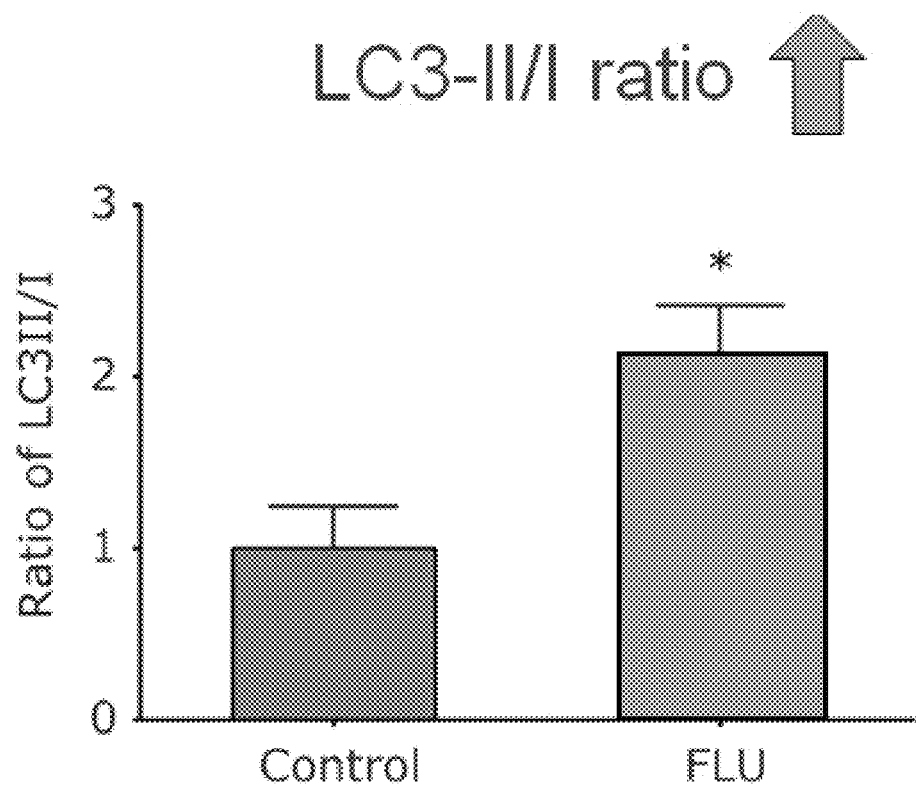
Figure 8C:
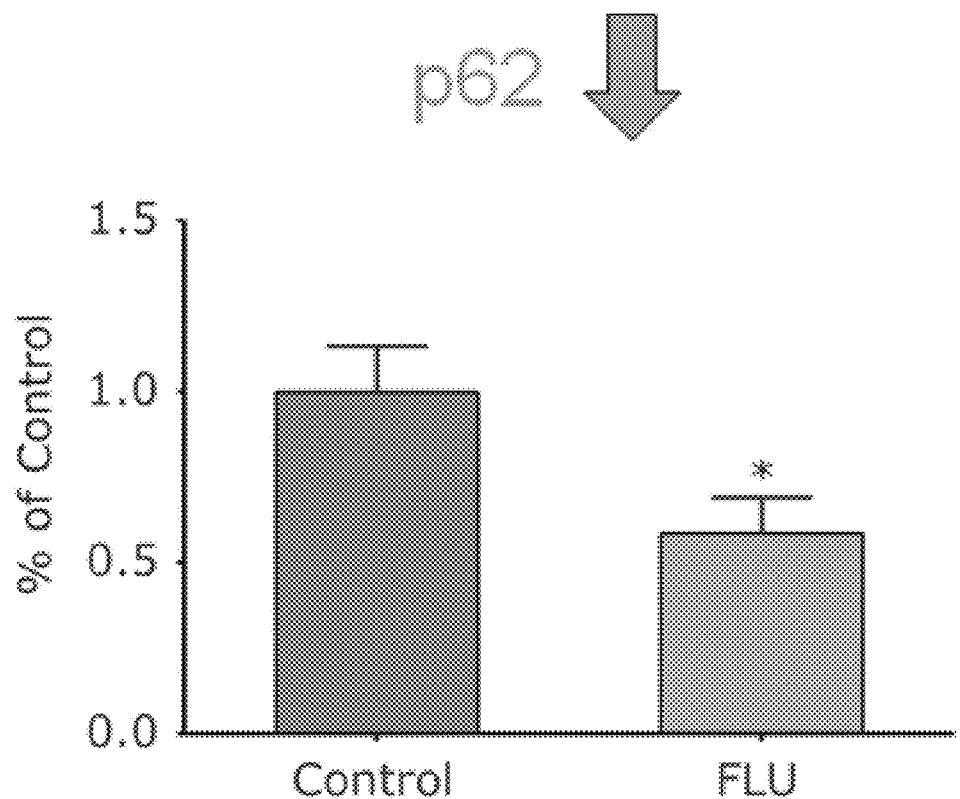

Fluphenazine and other phenothiazines reduce misfolded AT protein accumulation in a dose and time-dependent manner (FIG. 5B). Fluphenazine reduces mutant AT accumulation in the mouse model of ATD (FIG. 6A-FIG. 6E). Fluphenazine enhances autophagic flux in the liver (FIG. 7A-FIG. 7B).

Amlodipine alone or in combination with prochlorperazine reduces mutant AT accumulation. The combination of amlodipine and prochlorperazine is synergistic as shown by isobologram analysis (FIG. 8A-FIG. 8I).

Figures 9, 10A:
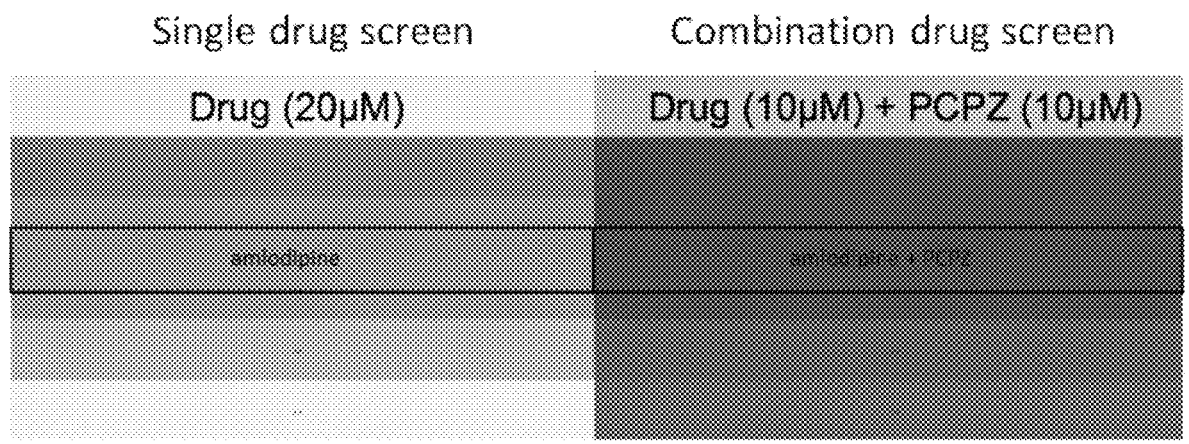
FIG. 9 depicts the strategy for combination drug screening. To identify synergistic drug combinations, we performed drug screens using single drugs or single drugs in combination with prochlorperazine. The red bars represent heat maps of drug activity. The more active drugs and drug combinations are depicted in darker shades of red. For example, amlodipine alone at 20 µM had modest activity in reducing mutant AT accumulation. However, amlodipine and prochlorperazine (PCPZ) in combination at lower concentrations had a significantly higher activity in reducing mutant AT accumulation.
FIG. 10A, FIG. 10B, and FIG. 10C shows data demonstrating that amlodipine and prochlorperazine combination acts synergistically to reduce mutant AT accumulation.
Figure 10B:
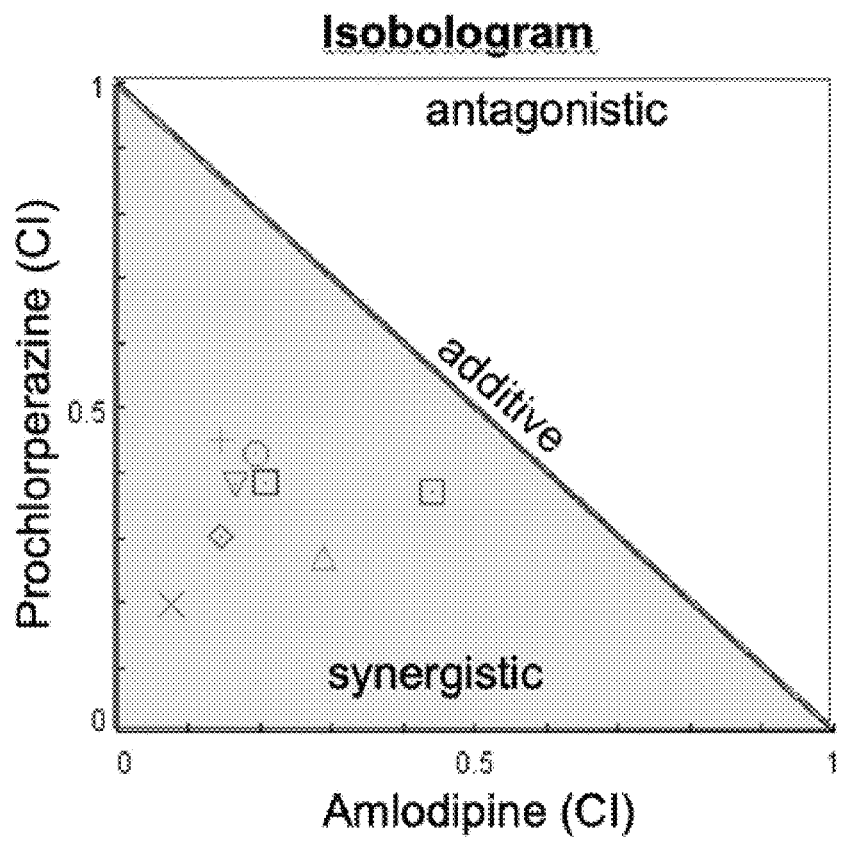
Figure 10C:
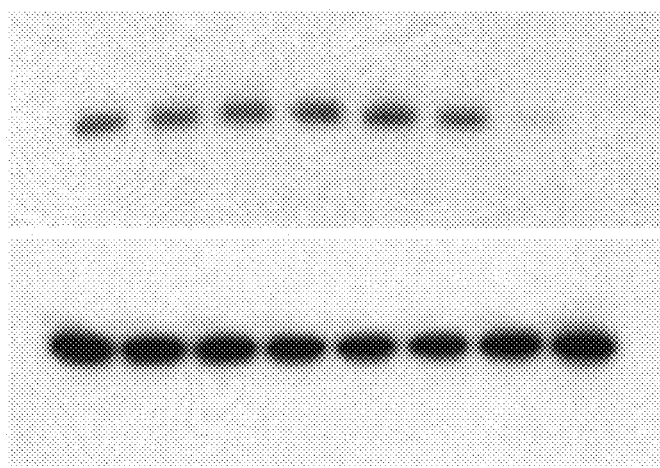
Figure 11A:
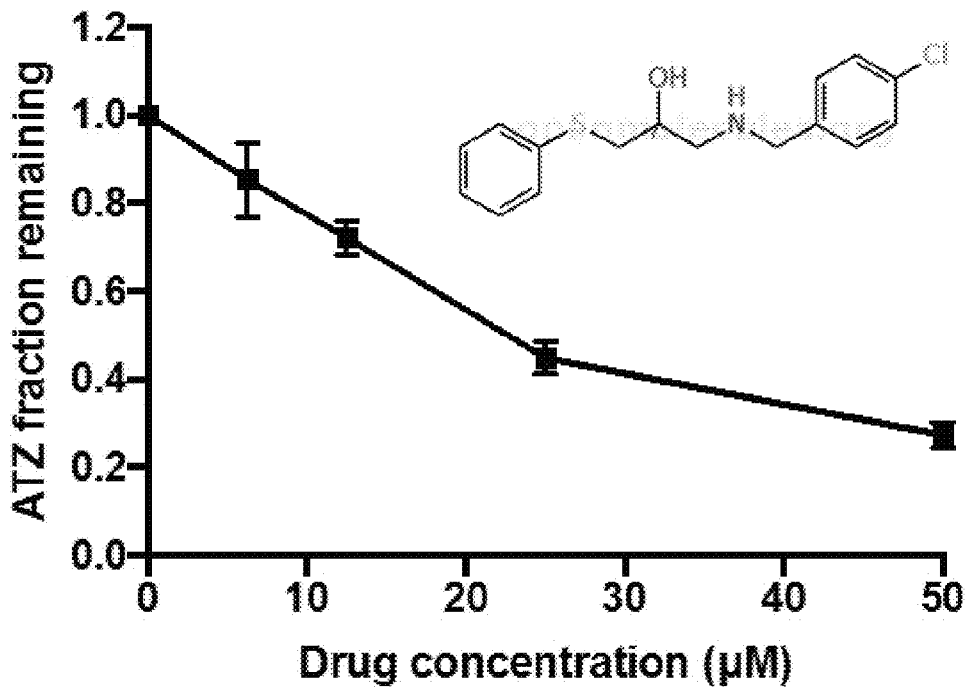
FIG. 11A and FIG. 11B examples of beta-amino alcohols and aryl piperazines in reducing AT accumulation.
Figure 11B:
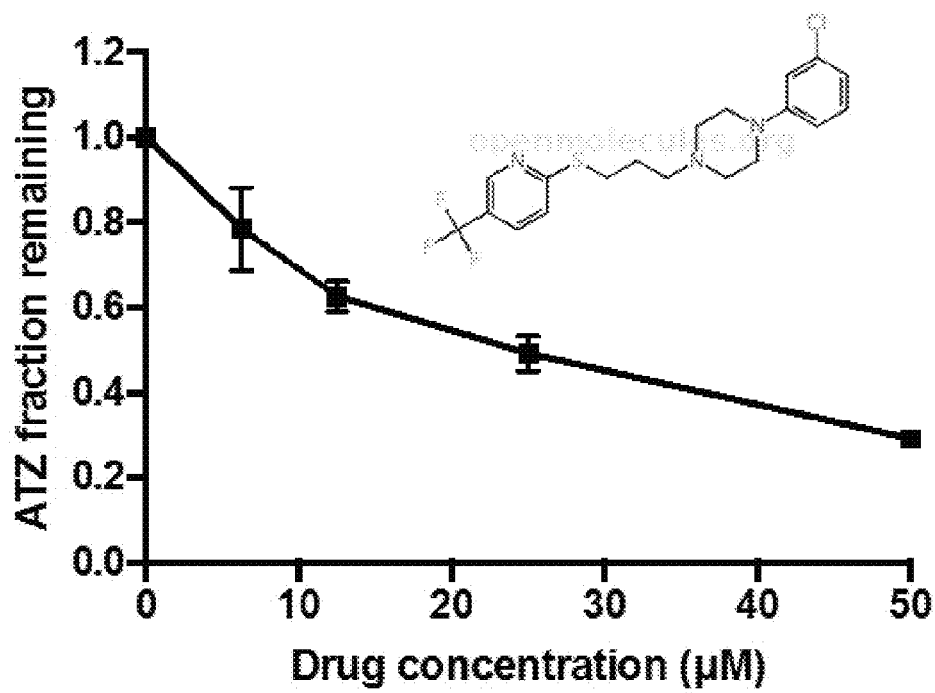

RDR 03172 and AW00794 reduce mutant AT protein accumulation (FIG. 9A and FIG. 9B).

TABLE 1

| Exemplary drug combinations: |
| --- |
| Prochlorperazine + Amlodipine |
| Prochlorperazine + Nilvadipine |
| Prochlorperazine + Alexidine (or chlorhexidine, hexetidine) |
| Prochlorperazine + Auranofin |
| Prochlorperazine + Sertraline |
| Prochlorperazine + Toremifene |
| Prochlorperazine + Perhexiline |
| Prochlorperazine + Aprepitant |
| Prochlorperazine + Desloratadine |
| Desloratadine + Amlodipine |
| Amlodipine + Perhexiline |

What is claimed is:

1. A method for treating a subject having or suspected of having alpha-1-antitrypsin deficiency (ATD), wherein the subject has not developed hepatocellular carcinoma, the method comprising: administering to the subject a therapeutically effective amount of a composition comprising one or more of a proteotoxicity reducing agent selected from Tricyclic antipsychotics, Vasodilators, Antibiotics/Antiseptics, and Aryl piperazines.

2. The method of claim 1, wherein the composition comprises a Prochlorperazine and a second proteotoxicity reducing agent selected from Amlodipine, Nilvadipine, Alexidine, Chlorhexidine, Hexetidine, Auranofin, Sertraline, Toremifene, Perhexiline, Aprepitant, and Desloratadine.

3. The method of claim 1, wherein the composition comprises Amlodipine and a second proteotoxicity reducing agent selected from Amlodipine, Nilvadipine, Alexidine, Chlorhexidine, Hexetidine, Auranofin, Sertraline, Toremifene, Perhexiline, Aprepitant, and Desloratadine.

4. The method of claim 3, wherein the second proteotoxicity reducing agent is selected from Perhexiline and Desloratadine.

5. The method of claim 1, wherein alpha-1-antitrypsin Z misfolding or accumulation is reduced relative to an untreated subject.

6. The method of claim 1, wherein clearance of a misfolded or mutant protein alpha-1-antitrypsin Z from the liver is enhanced.

7. The method of claim 1, wherein autophagy in a hepatocyte having a misfolded or mutant alpha-1-antitrypsin Z is enhanced.

* * * * *